(12) United States Patent
O'Brien-Coon et al.

(10) Patent No.: US 11,490,987 B2
(45) Date of Patent: Nov. 8, 2022

(54) ULTRASOUND-DETECTABLE MARKERS, ULTRASOUND SYSTEM, AND METHODS FOR MONITORING VASCULAR FLOW AND PATENCY

(71) Applicant: The Johns Hopkins University, Baltimore, MD (US)

(72) Inventors: Devin O'Brien-Coon, Baltimore, MD (US); Kaitlyn Harfmann, Baltimore, MD (US); Ting Yu Lai, Baltimore, MD (US); David Narrow, Baltimore, MD (US); Adam Lightman, Baltimore, MD (US); Youseph Yazdi, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 93 days.

(21) Appl. No.: 17/191,347

(22) Filed: Mar. 3, 2021

(65) Prior Publication Data
US 2021/0219956 A1   Jul. 22, 2021

Related U.S. Application Data

(62) Division of application No. 14/761,694, filed as application No. PCT/US2014/012274 on Jan. 21, 2014, now Pat. No. 11,382,714.

(Continued)

(51) Int. Cl.
*A61B 8/00* (2006.01)
*A61B 8/08* (2006.01)
(Continued)

(52) U.S. Cl.
CPC ............ *A61B 90/39* (2016.02); *A61B 8/0841* (2013.01); *A61B 8/0891* (2013.01); *A61B 8/14* (2013.01);
(Continued)

(58) Field of Classification Search
None
See application file for complete search history.

(56) References Cited

U.S. PATENT DOCUMENTS 4,041,931 A * 8/1977 Elliott .................... A61B 17/11
                                                  24/549
4,202,349 A * 5/1980 Jones .................... A61B 6/504
                                                  604/362

(Continued)

OTHER PUBLICATIONS

Cutright et al., Degradation rates of polymers and copolymers of polylactic and polyglycolic acids. Oral Surg Oral Med Oral Pathol. Jan. 1974;37(1):142-52.

(Continued)

*Primary Examiner* — Colin T. Sakamoto
(74) *Attorney, Agent, or Firm* — Casimir Jones, S.C.; Jeffrey W. Childers

(57) ABSTRACT

An ultrasound-detectable marker, ultrasound system, and methods for monitoring vascular flow and patency is disclosed. The ultrasound-detectable marker comprises one or more resorbable polymers, one or more non-resorbable polymers, one or more non-polymeric materials, or any combinations thereof. The ultrasound-detectable marker is adapted for placement underneath, adjacent to, or above one or more vessels at a postoperative site, such as a vascular anastomosis site. Further, the ultrasound imaging system includes certain user guiding software and/or health analysis software for use with the ultrasound-detectable marker.

33 Claims, 19 Drawing Sheets

Related U.S. Application Data

(60) Provisional application No. 61/819,979, filed on May 6, 2013, provisional application No. 61/754,177, filed on Jan. 18, 2013.

(51) Int. Cl.
*A61B 8/14* (2006.01)
*A61B 90/00* (2016.01)

(52) U.S. Cl.
CPC ........... *A61B 8/4444* (2013.01); *A61B 8/4483* (2013.01); *A61B 8/463* (2013.01); *A61B 8/488* (2013.01); *A61B 8/5207* (2013.01); *A61B 2090/378* (2016.02); *A61B 2090/3908* (2016.02); *A61B 2090/3925* (2016.02); *A61B 2090/3991* (2016.02)

(56) References Cited

U.S. PATENT DOCUMENTS

| | | | | |
|---|---|---|---|---|
| 4,373,532 | A * | 2/1983 | Hill | A61B 90/39 600/458 |
| 4,693,237 | A * | 9/1987 | Hoffman | A61B 90/39 128/899 |
| 4,787,391 | A * | 11/1988 | Elefteriades | A61B 6/12 600/431 |
| 6,248,117 | B1 | 6/2001 | Blatter | |
| 6,270,458 | B1 | 8/2001 | Ofer | |
| 6,358,211 | B1 * | 3/2002 | Mamayek | A61B 8/0833 600/459 |
| 6,544,185 | B2 | 4/2003 | Montegrande | |
| 6,616,675 | B1 | 9/2003 | Evard et al. | |
| 7,047,063 | B2 | 5/2006 | Burbank et al. | |
| 8,219,182 | B2 | 7/2012 | Burbank et al. | |
| 9,669,113 | B1 * | 6/2017 | Sirimanne | A61K 49/006 |
| 9,820,824 | B2 * | 11/2017 | Jones | A61B 90/39 |
| 2002/0151797 | A1 * | 10/2002 | Montegrande | A61B 90/39 600/458 |
| 2002/0188196 | A1 | 12/2002 | Burbank et al. | |
| 2003/0009100 | A1 | 1/2003 | Derendorf et al. | |
| 2003/0139669 | A1 | 7/2003 | Montegrande | |
| 2003/0233101 | A1 | 12/2003 | Lubock et al. | |
| 2004/0260318 | A1 | 12/2004 | Hunter et al. | |
| 2005/0019262 | A1 * | 1/2005 | Chernomorsky | A61L 31/146 424/9.4 |
| 2005/0137448 | A1 | 6/2005 | Wingler et al. | |
| 2005/0273002 | A1 * | 12/2005 | Goosen | A61B 90/39 600/414 |
| 2006/0036159 | A1 | 2/2006 | Sirimanne et al. | |
| 2006/0155190 | A1 | 7/2006 | Burbank et al. | |
| 2006/0293581 | A1 | 12/2006 | Plewes et al. | |
| 2007/0135711 | A1 | 6/2007 | Chernomorsky et al. | |
| 2007/0276232 | A1 | 11/2007 | Towe | |
| 2009/0000629 | A1 * | 1/2009 | Hornscheidt | A61B 90/39 604/116 |
| 2009/0030309 | A1 * | 1/2009 | Jones | A61P 7/04 600/431 |
| 2010/0010341 | A1 | 1/2010 | Talpade et al. | |
| 2010/0234726 | A1 * | 9/2010 | Sirimanne | A61K 49/006 600/426 |
| 2011/0004094 | A1 | 1/2011 | Stubbs et al. | |
| 2011/0021888 | A1 * | 1/2011 | Sing | A61B 5/0507 600/562 |
| 2011/0313288 | A1 * | 12/2011 | Chi Sing | A61B 8/0825 600/437 |
| 2014/0275750 | A1 * | 9/2014 | Levine | A61F 2/0045 606/228 |

OTHER PUBLICATIONS

Gimbel et al., Monitoring partial and full venous outflow compromise in a rabbit skin flap model. Plast Reconstr Surg. Sep. 2009;124(3):796-803.

Harfmann et al., Disclosure Evaluation, Confidential Report for Invention Disclosure No. C12305. A guiding Indication System for Monitoring Vascular Flow and Patency under Ultrasound.

Ingraham et al., Radiology of foreign bodies: how do we image them? Emerg Radiol. Aug. 2015;22(4):425-30.

Makadia et al., Poly Lactic-co-Glycolic Acid (PLGA) as Biodegradable Controlled Drug Delivery Carrier. Polymers (Basel). Sep. 1, 2011;3(3):1377-1397.

Smit et al., Advancements in free flap monitoring in the last decade: a critical review. Plast Reconstr Surg. Jan. 2010;125(1): 177-185.

Towe, Piezoelectric contrast materials for ultrasound imaging, IEEE Transactions on Ultrasonics, Ferroelectrics, and Frequency Control. Sep. 2005.

International Search Report and Written Opinion dated Jan. 21, 2014 from PCT International Application No. PCT/US2014/012274.

The extended European search report dated Aug. 19, 2016 for a corresponding European application No. 14740843.9.

* cited by examiner

ULTRASOUND-DETECTABLE MARKERS, ULTRASOUND SYSTEM, AND METHODS FOR MONITORING VASCULAR FLOW AND PATENCY

TECHNICAL FIELD

The presently disclosed subject matter relates generally to noninvasive methods of monitoring the health of a postoperative site, such as an anastomosis site, and more particularly to an ultrasound-detectable marker, ultrasound system, and methods for monitoring vascular flow and patency at postoperative sites.

BACKGROUND

It often is desirable to monitor vascular flow and/or patency at a postoperative site, such as an anastomosis site, following surgery. Noninvasive methods, such as ultrasound imaging, are, in principle, suitable for use in monitoring vascular flow and/or patency of anastomosis sites. Such monitoring, however, can be challenging because, for example, of (1) the difficulty in locating the postoperative site and (2) the difficulty in maintaining a linear orientation of the vessels of interest to obtain a useful image.

SUMMARY

In some aspects, the presently disclosed subject matter provides an ultrasound-detectable markers for monitoring postoperative site, such as a vascular anastomosis site, wherein the markers comprise one or more resorbable polymers, one or more non-resorbable polymers, one or more non-polymeric materials, or any combinations thereof; and wherein the markers are adapted for placement underneath, adjacent to, or above one or more vessels at a postoperative site, such as a vascular anastomosis site.

In other aspects, the presently disclosed subject matter provides a method for monitoring a postoperative site, the method comprising: (a) providing a marker comprising one or more resorbable polymers, one or more non-resorbable polymers, one or more non-polymeric materials, or any combinations thereof, wherein the marker is adapted for placement underneath, adjacent to, or above one or more vessels at a postoperative site; (b) placing the marker underneath, adjacent to, or above at least one vessel during or after surgery; and (c) using a software algorithm to guide a user with an ultrasound probe to the location of the marker post-surgery.

In further aspects, the presently disclosed subject matter provides a method for orienting one or more vessels linearly in a plane during surgery, the method comprising: (a) providing a marker comprising one or more resorbable polymers, one or more non-resorbable polymers, one or more non-polymeric materials, or any combinations thereof, wherein the marker is adapted for placement underneath, adjacent to, or above one or more vessels at a postoperative site; (b) placing the marker in a subject during surgery; and (c) placing the one or more vessels on the marker; and wherein the one or more vessels are oriented linearly in a plane after being placed on the marker.

Certain aspects of the presently disclosed subject matter having been stated hereinabove, which are addressed in whole or in part by the presently disclosed subject matter, other aspects will become evident as the description proceeds when taken in connection with the accompanying Drawings as best described herein below.

BRIEF DESCRIPTION OF THE DRAWINGS

Figure 1:
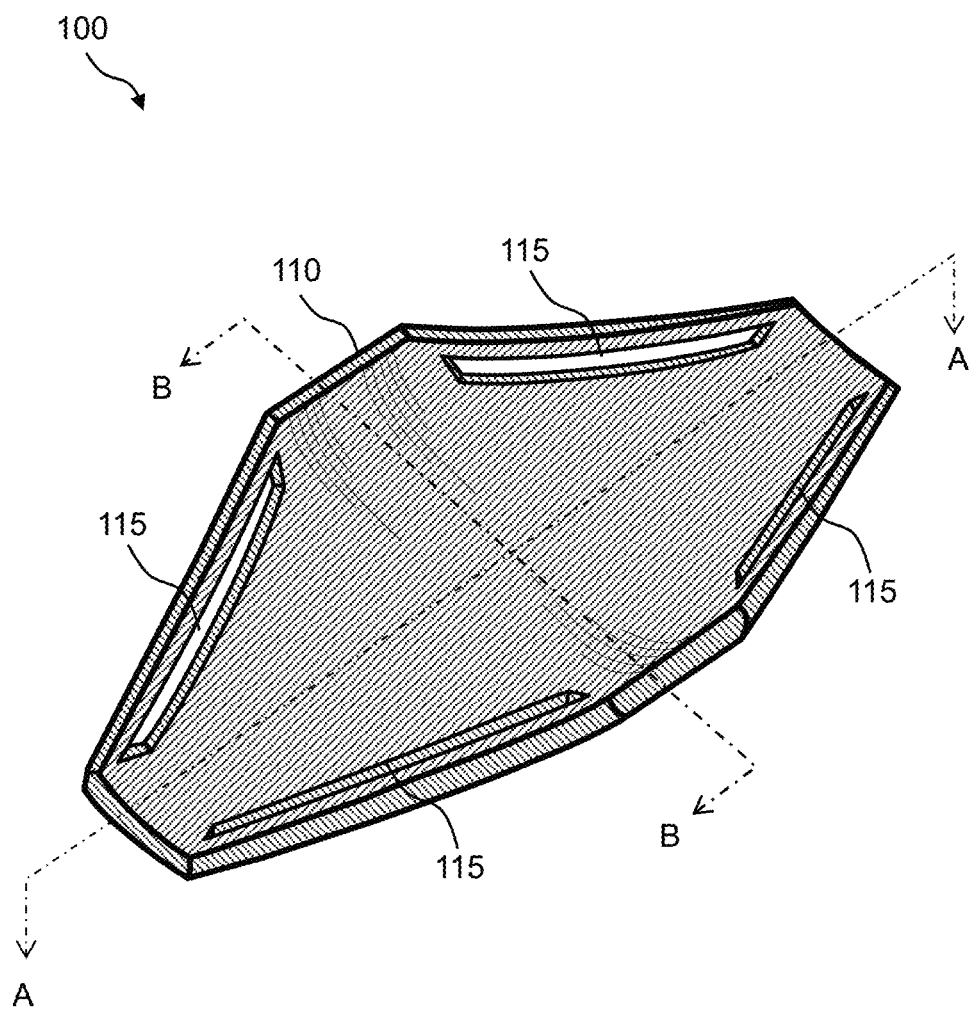
Figure 2:
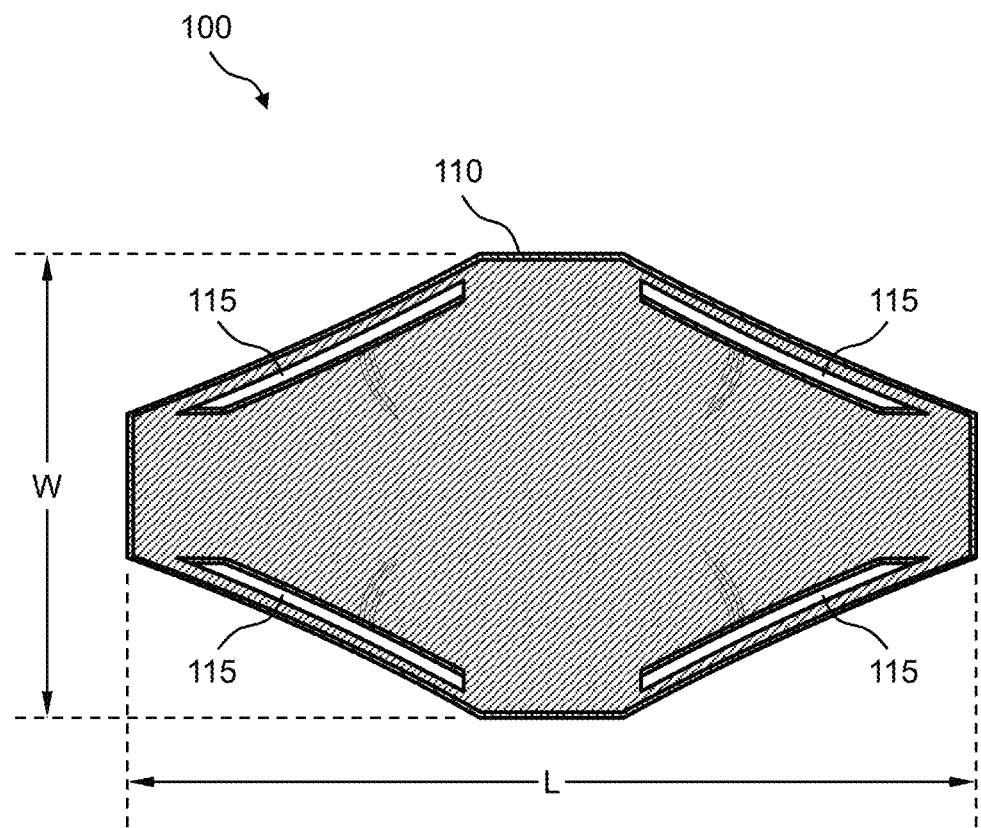
Figure 3A:
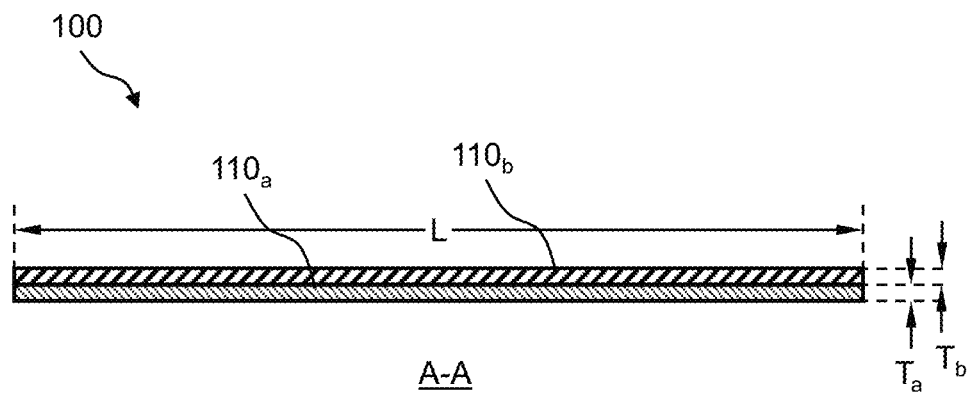
Figure 3B:
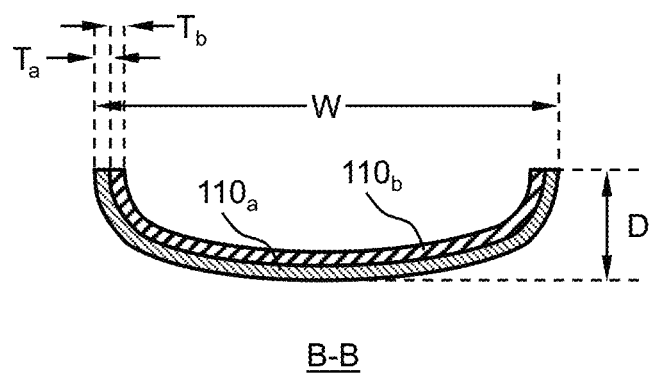
Figure 4:
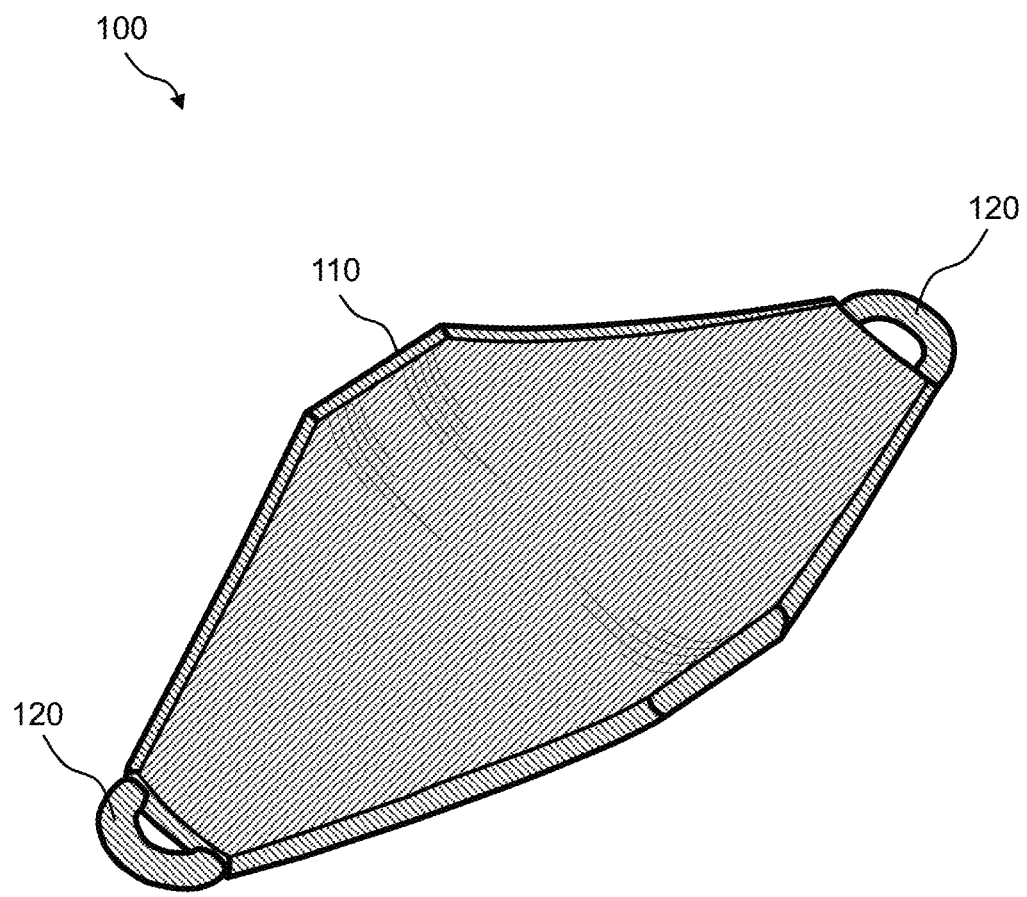
Figure 5:
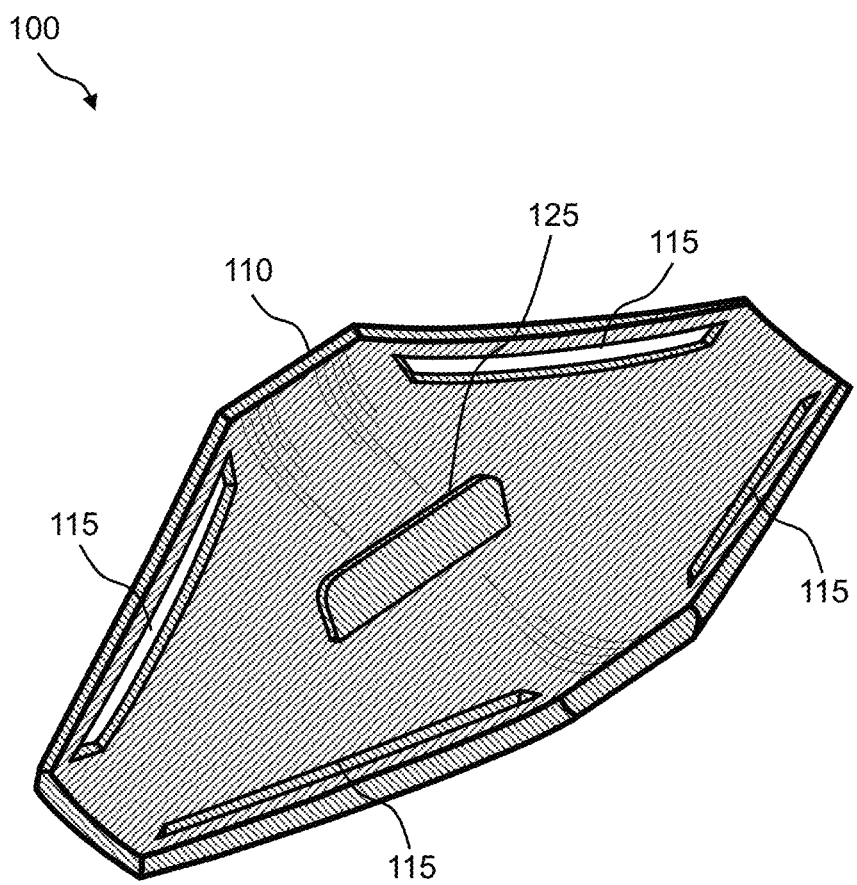
Figure 6:
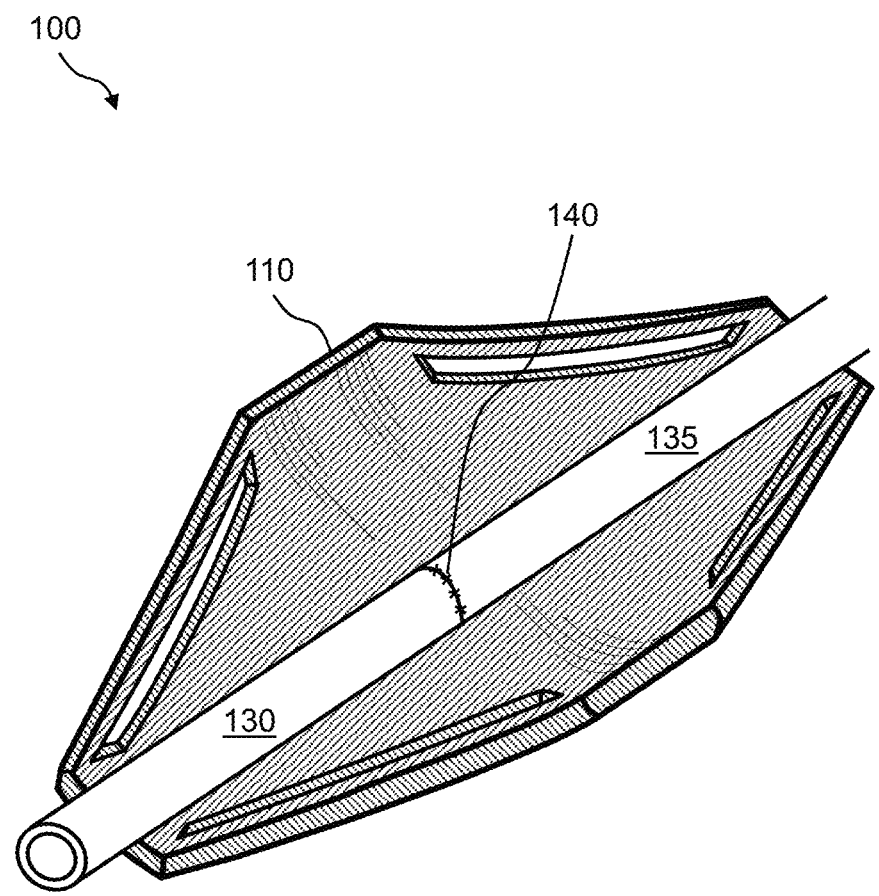
Figure 7:
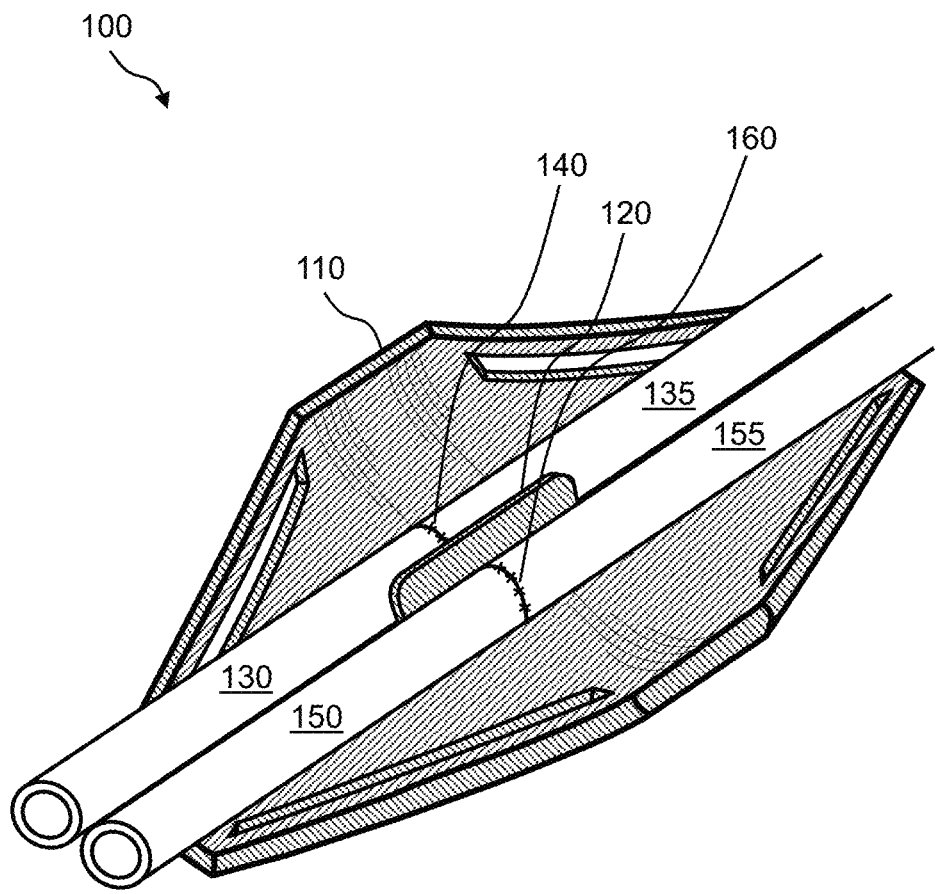
Figure 8:
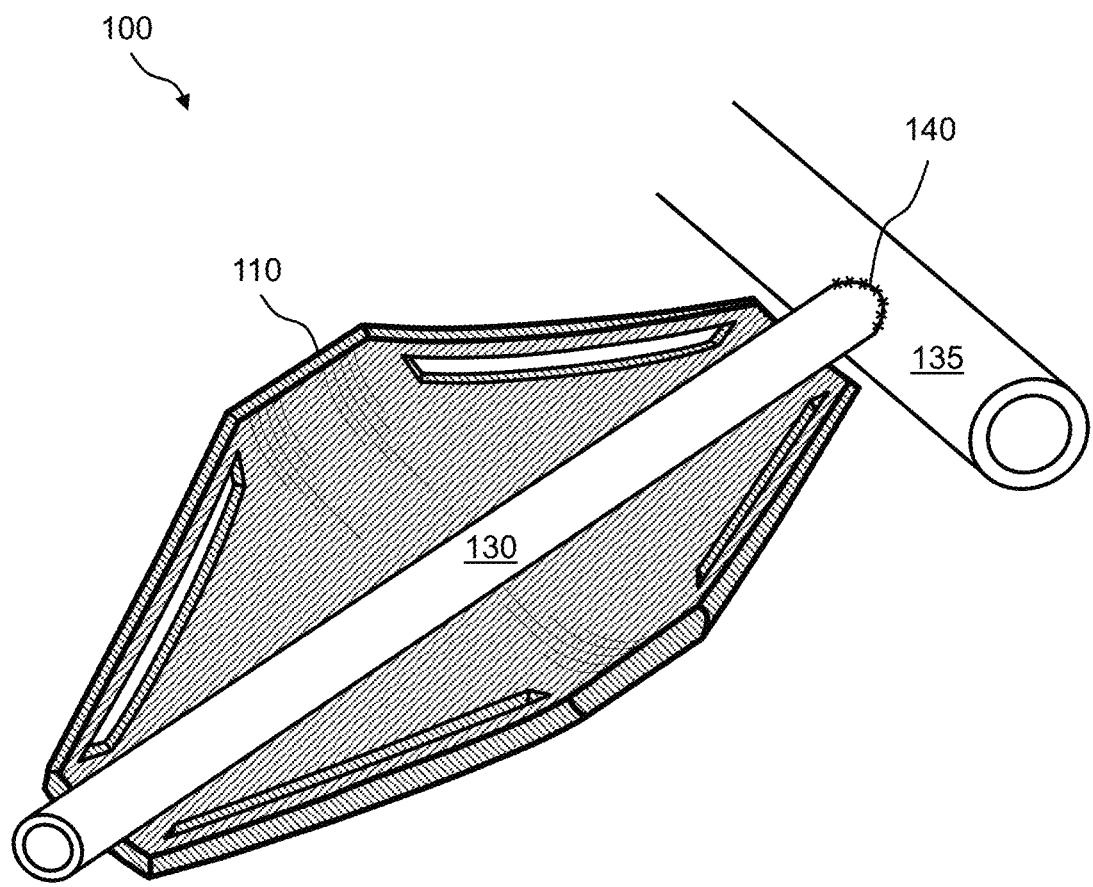
Figure 9:
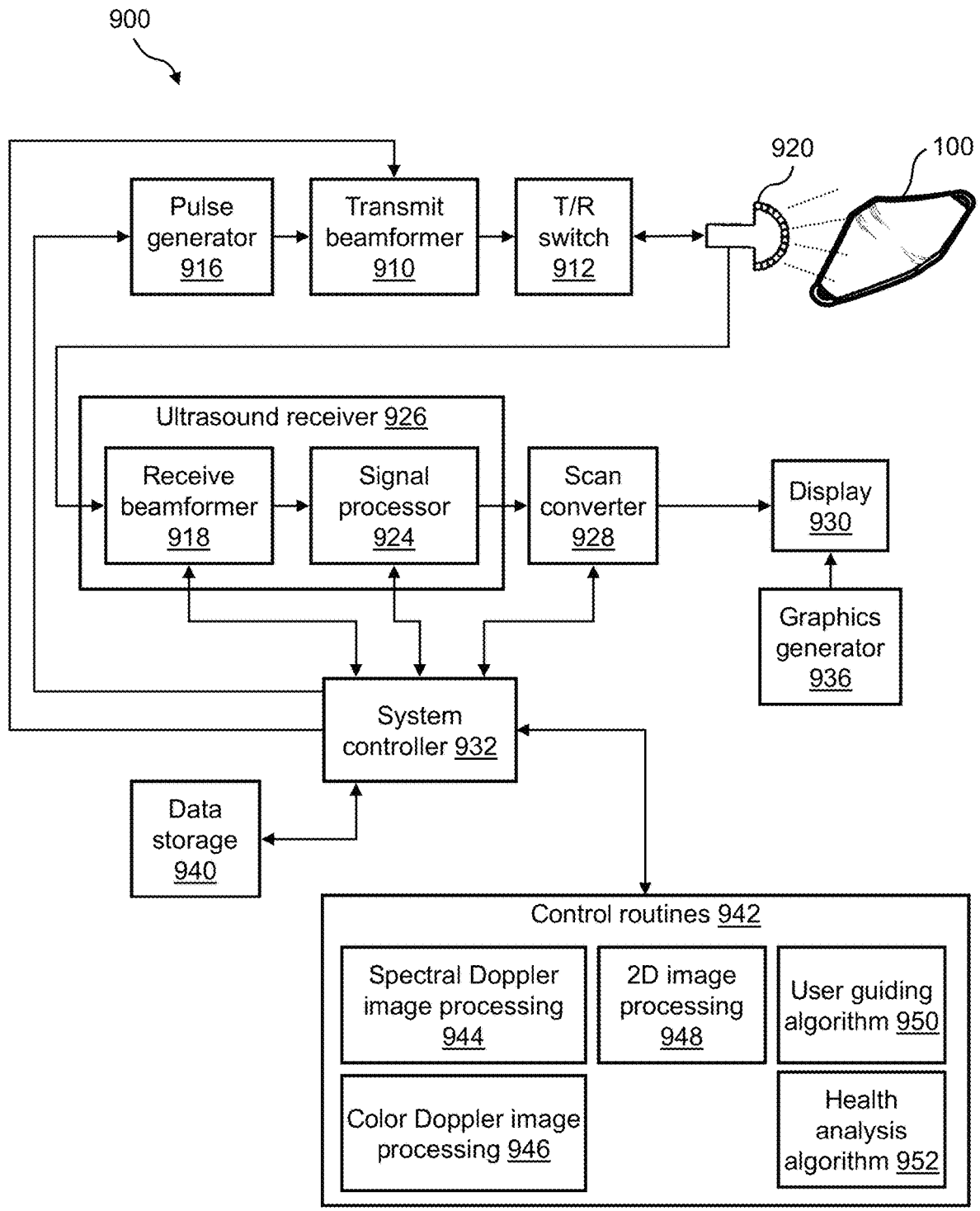
Figure 10:
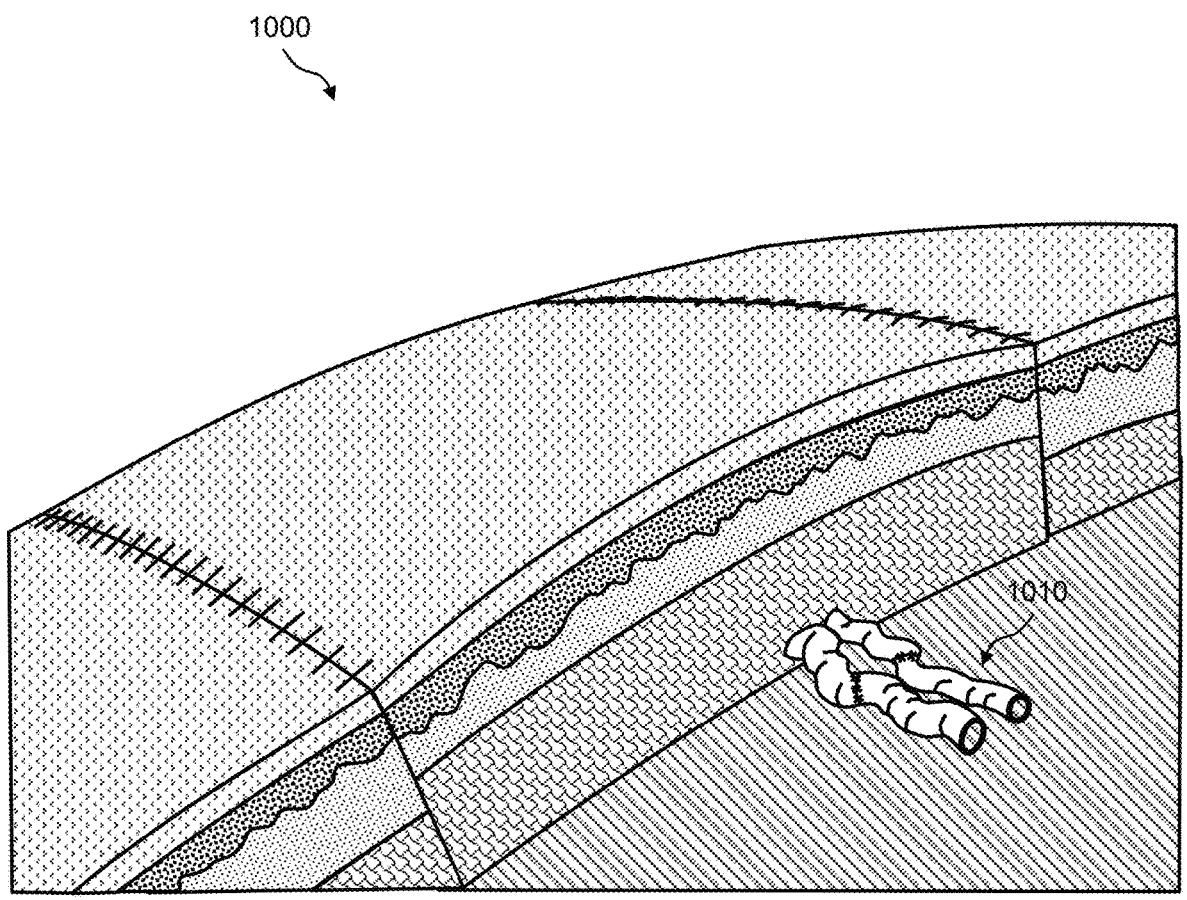
Figure 11:
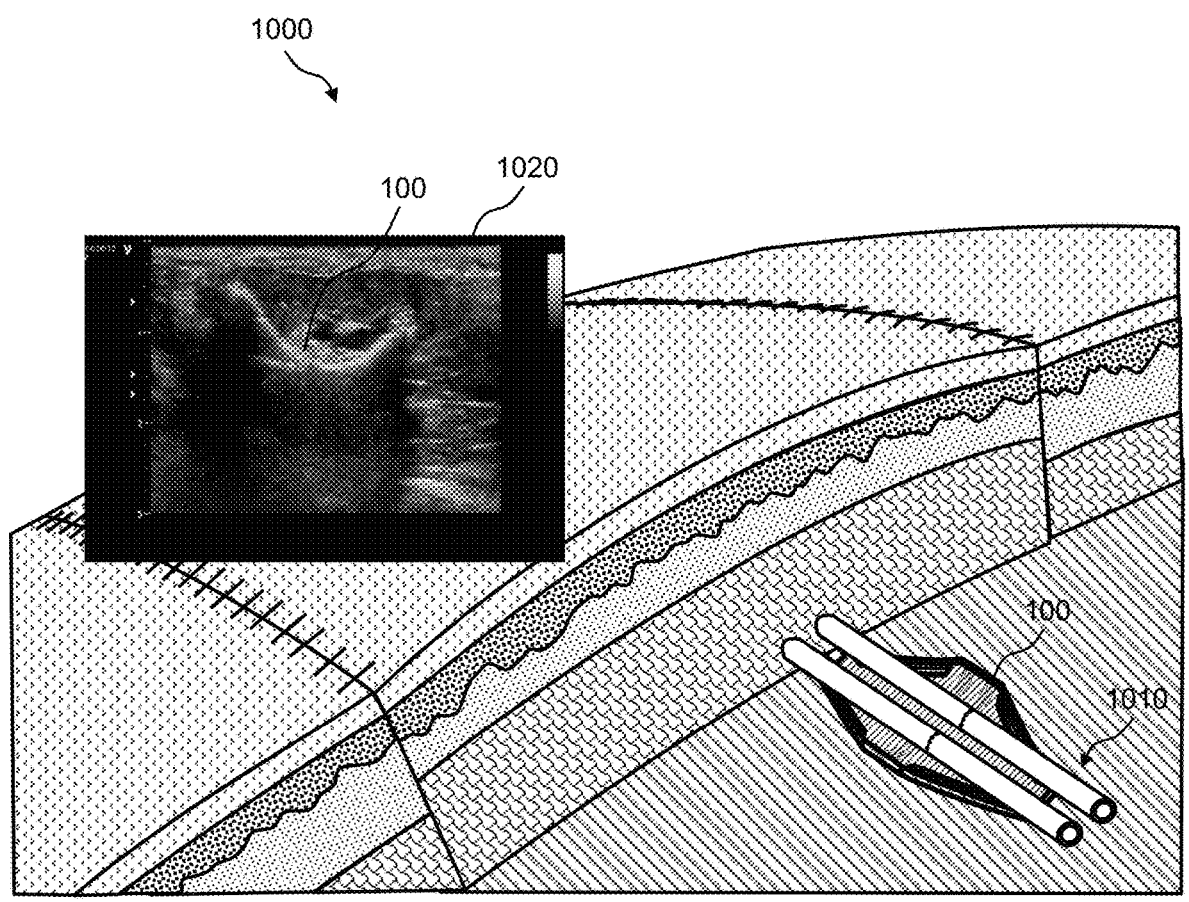
Figure 12:
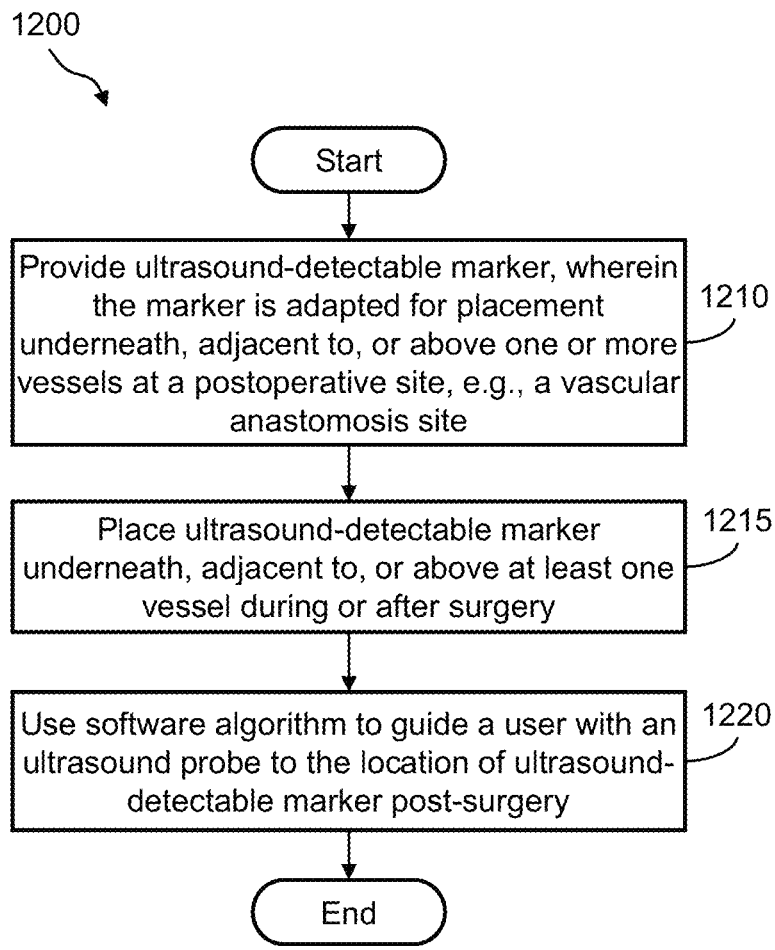
Figure 13:
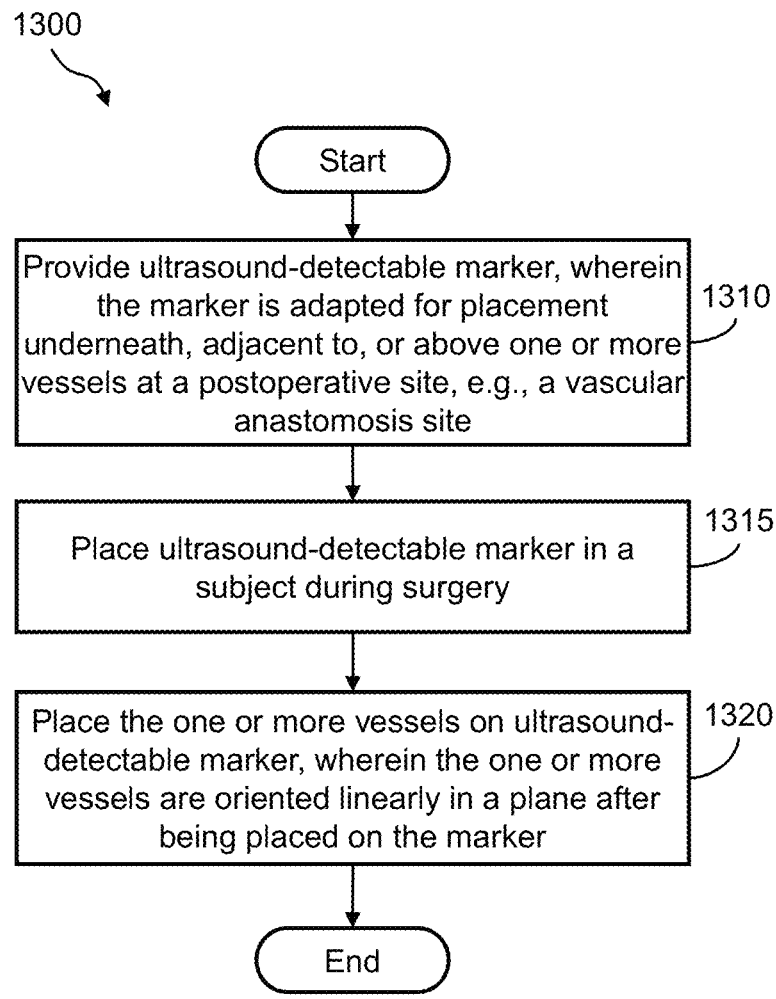
Figure 14:
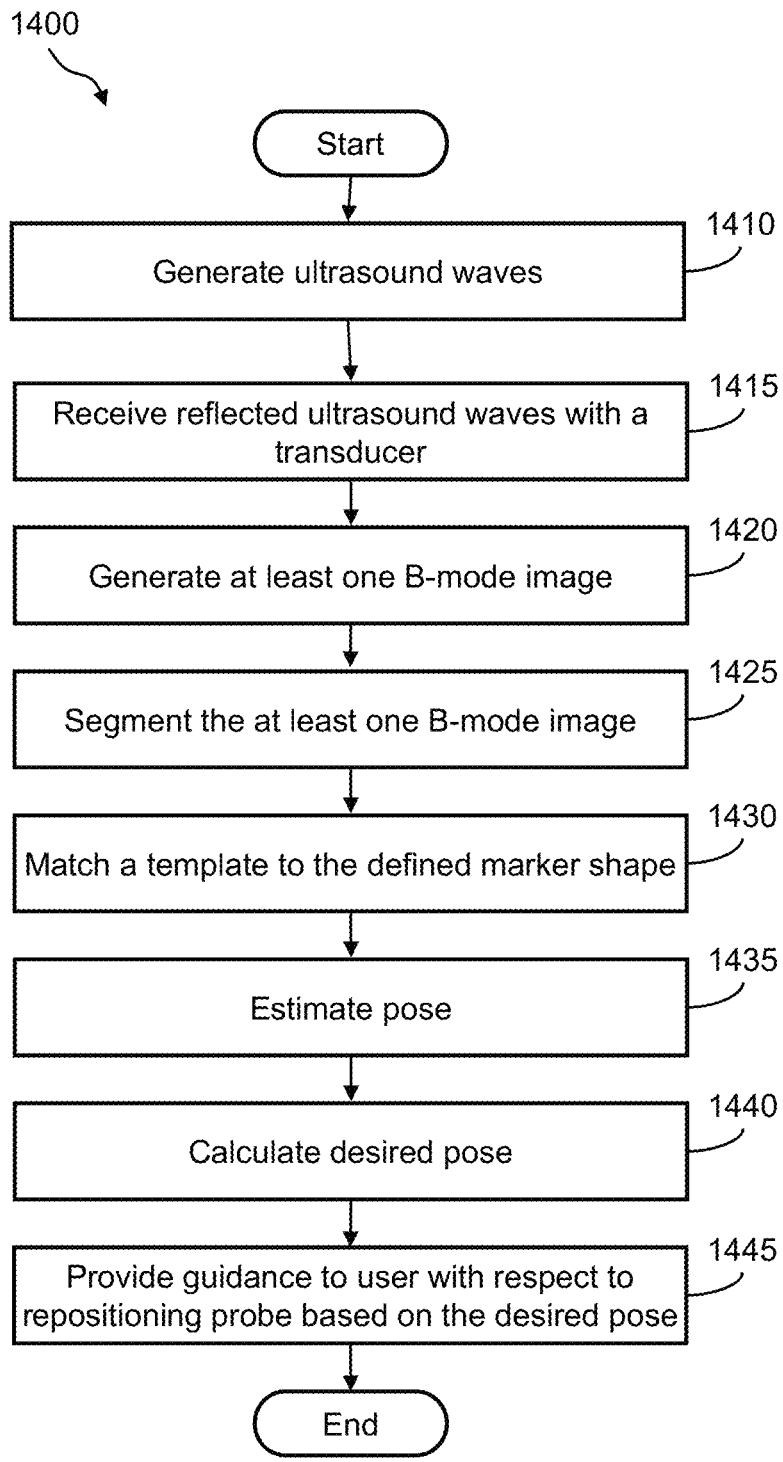
Figure 15:
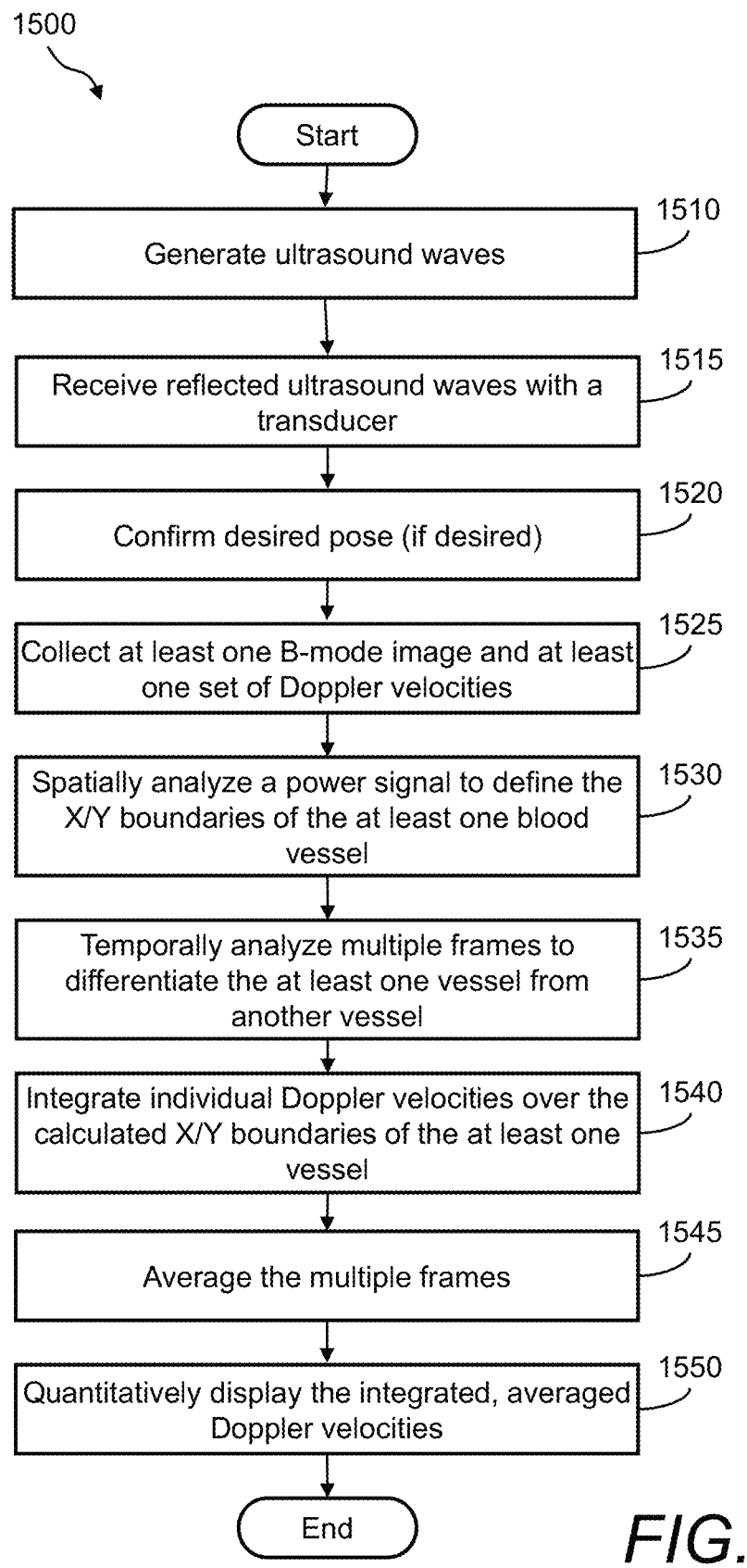

Having thus described the presently disclosed subject matter in general terms, reference will now be made to the accompanying Drawings, which are not necessarily drawn to scale, and wherein:

FIG. 1 illustrates a perspective view of an example of the presently disclosed ultrasound-detectable marker, wherein the ultrasound-detectable marker includes slits;

FIG. 2 illustrates a plan view of the ultrasound-detectable marker including slits shown in FIG. 1;

FIG. 3A and FIG. 3B illustrate cross-sectional views of the ultrasound-detectable marker shown in FIG. 1;

FIG. 4 illustrates a perspective view of another example of the presently disclosed ultrasound-detectable marker, wherein the ultrasound-detectable marker includes eyelets;

FIG. 5 illustrates a perspective view of the presently disclosed ultrasound-detectable marker that further comprises a divider;

FIG. 6, FIG. 7, and FIG. 8 illustrate perspective views of examples of the presently disclosed ultrasound-detectable marker when in use;

FIG. 6 illustrates a perspective view of an end-to-end vascular anastomosis site oriented on a presently disclosed ultrasound-detectable marker;

FIG. 7 illustrates a perspective view of a side-to-side vascular anastomosis site oriented on a presently disclosed ultrasound-detectable marker;

FIG. 8 illustrates a perspective view of an end-to-side vascular anastomosis site oriented on a presently disclosed ultrasound-detectable marker;

FIG. 9 illustrates a block diagram of an example of an ultrasound imaging system that includes certain user guiding software and health analysis software for use with the ultrasound-detectable markers;

FIG. 10 is a representation depicting the tendency of postoperative vessels to naturally adopt a tortuous course, which is not amenable to cross-sectional visualization and imaging; and FIG. 11 is a representation illustrating that the presently disclosed closed ultrasound-detectable marker can be used to align the vessels to permit visualization;

FIG. 12 illustrates a flow diagram of an example of a method of monitoring a vascular anastomosis site during surgery using the ultrasound-detectable marker and the ultrasound imaging system;

FIG. 13 illustrates a flow diagram of an example of a method of orienting at least one vessel linearly in a plane during surgery using the ultrasound-detectable marker and the ultrasound imaging system;

FIG. 14 illustrates a flow diagram of an example of the process flow of the user guiding algorithm of the ultrasound imaging system;

FIG. 15 illustrates a flow diagram of an example of the process flow of the health analysis algorithm of the ultrasound imaging system; and FIG. 16, FIG. 17, FIG. 18, and FIG. 19 illustrate various views of yet other examples of the presently disclosed ultrasound-detectable marker.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides an ultrasound-detectable marker, ultrasound system, and methods for monitoring vascular flow and patency. In particular embodiments, ultrasound-detectable markers are provided that can be placed at a postoperative site, such as a vascular anastomosis site, and located via ultrasound during or after surgery. The ultrasound-detectable markers provide a mechanism by which the postoperative site, such as a vascular anastomosis site, may be easily located and then the health of the postoperative site can be assessed. In other embodiments, an ultrasound imaging system is provided that includes certain user guiding software and/or health analysis software for use with the ultrasound-detectable marker, whereby the ultrasound imaging system and the ultrasound-detectable marker can be used for monitoring vascular flow and patency postoperatively.

As used herein, the term "vasculature" generally means any part of the circulatory system. More particularly, the term "vasculature" can include the arrangement of blood vessels in the body or in an organ or body part.

As used herein, the term "patency" means the state of being open, unobstructed, or unblocked, for example, a vein or artery that is free of obstruction.

I. Markers for Monitoring Vascular Flow and Patency Under Ultrasound

Referring now to FIG. 1 and FIG. 2 is a perspective view and a plan view, respectively, of an example of the presently disclosed ultrasound-detectable marker 100. Further, FIG. 3A shows a cross-sectional view of the ultrasound-detectable marker 100 taken along line A-A of FIG. 1 and FIG. 3B shows a cross-sectional view of the ultrasound-detectable marker 100 taken along line B-B of FIG. 1.

The ultrasound-detectable marker 100 comprises a body 110 that is, for example, a plate having a substantially half-pipe or leaf shape (see FIG. 3B). In one example, the footprint of the ultrasound-detectable marker 100 is substantially octagonal, as shown in FIG. 1 and FIG. 2. However, the footprint of the ultrasound-detectable marker 100 is not limited to octagonal. The footprint of the ultrasound-detectable marker 100 can be any shape, including, but not limited to, ovular, circular, hexagonal, octagonal, square, rectangular, and the like.

The body 110 of the ultrasound-detectable marker 100 comprises, for example, one or more resorbable polymers. However, the ultrasound-detectable marker 100 is not limited to comprising resorbable polymers only. The body 110 of the ultrasound-detectable marker 100 can include non-polymeric materials, such as metal clips, or a combination of both resorbable polymers and non-polymeric materials.

As used herein, the term "resorbable" refers to a material, such as a polymeric material, which can be broken down and assimilated into a body. Representative resorbable polymers suitable for use with the presently disclosed markers include, but are not limited to, poly(lactic-co-glycolic acid) (PLGA), polylactides (PLAs), including poly(L-lactide), poly(D-lactide), and poly(DL-lactide), polyglycolide (PGA), polycaprolactone, L-lactide/DL-lactide copolymers, L-lactide/D-lactide copolymers, L-lactide/glycolide copolymers, L-lactide/caprolactone, DL-lactide/glycolide copolymers, and polyhydroxyalkanoates (PHAs), such as polyhydroxybutyrate (PHB), which include poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), polydioxanone, hyaluronate, chitin, cellulose, collagen, polyethylene glycol, and copolymers thereof.

More particularly, in some embodiments, the presently disclosed marker comprises one or more resorbable polymers selected from the group consisting of PLA and PGA. In further embodiments, the one or more resorbable polymers is PLGA. In still further embodiments, the presently disclosed marker comprises two or more resorbable polymer layers, wherein at least two resorbable polymer layers do not comprise the same resorbable polymer. In other embodiments, the two resorbable polymer layers comprise PLA and PGA.

In some embodiments, the ultrasound-detectable marker 100 comprises a varying ratio of two or more resorbable polymers. In other embodiments, the ultrasound-detectable marker 100 comprises a varying ratio of PLA:PGA.

In some embodiments, the ultrasound-detectable marker 100 comprises two or more resorbable polymer layers and/or a varying ratio of two or more resorbable polymers, and the presence of two or more resorbable polymer layers and/or a varying ratio of two or more resorbable polymers creates an impedance change throughout the ultrasound-detectable marker 100.

In still further embodiments of the presently disclosed ultrasound-detectable marker 100, microbubbles can be introduced in the polymer to create impedance changes throughout the volume of the ultrasound-detectable marker 100.

By "impedance changes throughout", it is meant that the majority of the ultrasound-detectable marker 100 has variations resulting in an impedance change. For example, more than about 50% to 100% of the ultrasound-detectable marker 100 has variations, such as more than 50%, 60%, 70%, 80%, 90%, or 99% of the ultrasound-detectable marker 100. Variations in the ultrasound-detectable marker 100 can be made by manufacturing the ultrasound-detectable marker 100 in layers, by varying the ratios of at least two polymers in the ultrasound-detectable marker 100, by adding microbubbles to the ultrasound-detectable marker 100, and the like.

Such variations resulting in impedance changes allow the ultrasound-detectable marker 100 to be monitored using an ultrasound apparatus. Using the presently disclosed methods (see FIG. 12, FIG. 13, FIG. 14, FIG. 15), the site of a previous or ongoing surgery can be found easily and a vessel at the site of surgery can be imaged easily, such as by ultrasound imaging. In addition, the specific site of a vascular anastomosis can be determined, monitored, and evaluated for the presence of patency or blood clotting.

In further embodiments, the ultrasound-detectable marker 100 comprises one or more non-resorbable polymers. In particular embodiments, the one or more non-resorbable polymers is selected from the group consisting of polycarbonate, polyetheretherketone, polypropylene, silicone, polyethylene, and combinations thereof.

Referring again to FIG. 1 and FIG. 2, in some embodiments, the ultrasound-detectable marker 100 comprises one or more holes and/or slits 115 adapted to inform a geometric position. The holes or slits 115 can be cut through the volume of the ultrasound-detectable marker 100. In the example shown in FIG. 1 and FIG. 2, four slits 115 are provided along four respective edges of the body 110.

Adding holes and/or slits 115 in an asymmetric fashion to the ultrasound-detectable marker 100 aids the presently disclosed software algorithms (see FIG. 9) in determining the orientation of the ultrasound-detectable marker 100 in vivo. In other embodiments, eyelet holes can be added to the ultrasound-detectable marker 100 which can be used for attaching, e.g., by suturing, the ultrasound-detectable marker 100 to adjacent soft tissue. Accordingly, the ultrasound-detectable marker 100 comprises at least one eyelet hole adapted to secure the ultrasound-detectable marker 100 to soft tissue near the vascular anastomosis site. Namely, FIG. 4 shows another example of the ultrasound-detectable marker 100, wherein the ultrasound-detectable marker 100 includes an eyelet 120 at each end of the body 110, instead of the holes and/or slits 115. However, in yet other embodiments, the ultrasound-detectable marker 100 can include both holes and/or slits 115 and eyelets 120.

In some embodiments, the presently disclosed marker comprises a divider adapted to separate at least two blood vessels. Namely, FIG. 5 shows another example of the ultrasound-detectable marker 100, wherein the ultrasound-detectable marker 100 includes a divider 125 protruding from a center portion of the body 110. In further embodiments, the at least two blood vessels are an artery and a vein. In still further embodiments, the divider 125 ensures that the blood vessels are in parallel positions.

The ultrasound-detectable marker 100 can be scaled at a variety of sizes, which accommodate the variety of vessel sizes seen across different relevant medical applications. In representative embodiments, and referring again to FIG. 1, FIG. 2, FIG. 3A, and FIG. 3B, the ultrasound-detectable marker 100 has a length L, a width W, and a thickness T. Further, as shown in FIG. 3B, the substantially half-pipe or leaf shape of the body 110 has a depth D.

The length L of the ultrasound-detectable marker 100 can be, for example, from about 5 mm to about 80 mm. The width W of the ultrasound-detectable marker 100 can be, for example, from about 5 mm to about 60 mm. The thickness T of the ultrasound-detectable marker 100 can be, for example, from about 0.5 mm to about 8 mm. The depth D of the ultrasound-detectable marker 100 can be, for example, from about 5 mm to about 25 mm. In one example, the ultrasound-detectable marker 100 has a length L of about 40 mm, a width W of about 25 mm, a thickness T of about 2 mm, and a depth D of about 15 mm.

In some embodiments, the ultrasound-detectable marker 100 has a detectable in vivo lifetime during which the ultrasound-detectable marker 100 remains detectable by ultrasound. In other embodiments, the amount of time that the ultrasound-detectable marker 100 remains detectable depends on the type of material that the ultrasound-detectable marker 100 is constructed of, the thickness of the material, and the like. In further embodiments, the ultrasound-detectable marker 100 may remain detectable for days, weeks, months, or many years.

The ultrasound-detectable markers 100 shown in FIG. 1 through FIG. 5 are implantable resorbable polymeric markers that can be sutured to soft tissue via surgical sutures. These markers can be used to locate vessels of interest and to achieve the proper angle and slice of the vessel.

In certain surgeries, it is desirable to be able to monitor the site of surgery during the post-surgery healing period by a noninvasive method, such as ultrasound imaging. The ability to do so is particularly important for vascular surgeries. Examples of vascular surgeries include anastomoses, which are typically performed on blood vessels, such as arteries and veins.

As used herein, the term "anastomosis" refers to the joining together of two hollow structures, for example, two arteries or veins, to restore continuity after resection, e.g., a surgical procedure to remove part of an organ or a tumor or normal tissue around the margin of the tumor, or to bypass unresectable diseased tissue. Such procedures can be performed with suture material, mechanical staplers, or biodegradable or resorbable glues.

An anastomosis can be end-to-end, side-to-side, or end-to-side depending on the circumstances of the required reconstruction or bypass procedure. By way of example, FIG. 6, FIG. 7, and FIG. 8 illustrate perspective views of examples of the presently disclosed ultrasound-detectable marker 100 when in use. Namely, FIG. 6 shows an end-to-end anastomosis in relation to the ultrasound-detectable marker 100, wherein the end of a first vessel 130 is joined to the end of a second vessel 135 and wherein a joint 140 is formed, for example, using sutures. FIG. 7 shows first vessel 130 joined end-to-end with second vessel 135. Further, FIG. 7 shows a third vessel 150 is joined to the end of a fourth vessel 155, wherein a joint 160 is formed, for example, using sutures. In this example, first vessel 130 and second vessel 135 are separated from and held parallel to third vessel 150 and fourth vessel 155 via the divider 125 of the ultrasound-detectable marker 100. FIG. 8 shows an end-to-side anastomosis in relation to the ultrasound-detectable marker 100, wherein the end of the first vessel 130 is joined to the side of the second vessel 135 and wherein the joint 140 is formed, for example, using sutures.

Further, the term "reanastomosis" refers to a surgical reconnection, for example, to reverse a prior surgery to disconnect an anatomical anastomosis, e.g., tubal reversal after tubal ligation, or to reverse a vasectomy. The term "anastomosis" as used herein includes "reanastomosis."

Most vascular procedures, including, but not limited to, arterial bypass operations, e.g., a coronary artery bypass, aneurysmectomies, and solid organ transplants, require vascular anastomoses. In other examples, an anastomosis connecting an artery to a vein also is used to create an arteriovenous fistula, e.g., a cimino fistula, as an access for hemodialysis in patients having end stage renal failure.

Further, resections of gastrointestinal organs, including the esophagus, stomach, small bowel, large bowel, bile ducts, and pancreas, are followed by anastomoses to restore continuity. Such resections include bypass operations of the GI tract during bariatric surgery.

In yet further examples, surgical procedures, such as radical prostatectomy and radical cystectomy, involving the urinary tract, including ureters, urinary bladder, and urethra, can require anastomosis of the bladder to the urethra to restore continuity.

The presently disclosed ultrasound-detectable marker 100 and methods of use thereof localize postoperative vessels under ultrasound; provide feedback to the user regarding the location of these vessels; provide imagery of vasculature to determine patency; and provide quantitative analysis of vascular flow to monitor vascular health.

Further, the geometry of the presently disclosed ultrasound-detectable marker 100 provides multi-axis feedback to guide the user to the desired probe orientation and view (i.e., both translational and rotational movements of the probe).

In some embodiments, the presently disclosed ultrasound-detectable marker 100 provides an implantable, resorbable marker for monitoring blood vessels after or during post-surgical reconstruction. The ultrasound-detectable marker 100 serves as an indicator, which provides echogenic contrast when viewed under ultrasound, thus allowing medical personnel, e.g., an ultrasound technician, nurse, or doctor, to effectively and accurately locate the anastomosis site. In addition, the presently disclosed ultrasound-detectable marker 100 aids in maintaining a linear orientation of the vessel(s) so that the vessel(s) can be imaged. If the vessel is not traveling linearly in a plane, such as if it is coiled in an "S" shape, for example, the vessel will not be able to be clearly imaged, such as by ultrasound imaging.

II. System for Monitoring Vascular Flow and Patency Under Ultrasound

In other embodiments, the presently disclosed subject matter includes software as described herein below with reference to FIG. 9, which provides images and quantitative analysis of the vasculature to determine patency and volumetric flow rate, thus indicating the overall health of the tissue site.

Accordingly, the presently disclosed subject matter provides an ultrasound-detectable marker 100 for monitoring a postoperative site, such as a vascular anastomosis site, wherein the ultrasound-detectable marker 100 comprises one or more resorbable polymers, one or more non-resorbable polymers, one or more non-polymeric materials, or any combinations thereof; and wherein the marker is adapted for placement underneath, adjacent to, or above one or more vessels at the postoperative site.

FIG. 9 is a block diagram illustrating an ultrasound imaging system 900 that includes certain user guiding software and health analysis software for use with the ultrasound-detectable markers 100. It will be understood by those having ordinary skill in the art that the ultrasound imaging system 900, as illustrated in FIG. 9, and the operation thereof as described below, is intended to be generally representative of such systems and that any particular system may differ significantly from that shown in FIG. 9. The ultrasound imaging system 900 includes a transmit beamformer 910 coupled through a transmit receive (T/R) switch 912 to an ultrasound probe 950. While the ultrasound probe 950 may be any transducer probe, in one example, the ultrasound probe 950 is a matrix transducer probe.

In one example, the T/R switch 912 includes one switch element for each transducer element. In another example, the ultrasound probe 950 includes multiplexing circuitry, or the like, to reduce the number of required switches. The transmit beamformer 910 receives pulsed sequences from a pulse generator 916. The ultrasound probe 950, energized by the transmit beamformer 910, transmits ultrasound energy into a region of interest in a patient's body and receives reflected ultrasound energy, commonly referred to as echoes, from various structures and organs within the body. As is known by those having ordinary skill in the art, by appropriately delaying the waveforms applied to each transducer element by the transmit beamformer 910, a focused ultrasound beam may be transmitted from the ultrasound probe 950.

The ultrasound probe 950 is also coupled, through the T/R switch 912, to a receive beamformer 918. Ultrasound energy from a given point within the patient's body is received by the transducer elements at different times. The transducer elements convert the received ultrasound energy to transducer signals which may be amplified, individually delayed and then summed by the receive beamformer 918 to provide a beamformed signal that represents the received ultrasound levels along a desired receive line ("beam"). The receive beamformer 918 may be a digital beamformer including an analog-to-digital converter for converting the transducer signals to digital values, or may be an analog beamformer. As known to those having ordinary skill in the art, the delays applied to the transducer signals may be varied during reception of ultrasound energy to effect dynamic focusing. The process is repeated for multiple scan lines to create a frame of data for generating an image of the region of interest in the patient's body.

The receive beamformed signals are then applied to a signal processor 924, which processes the beamformed signal for improved image quality. The receive beamformer 918 and the signal processor 924 comprise an ultrasound receiver 926. The output of the signal processor 924 is supplied to a scan converter 928, which converts sector scan and other scan pattern signals to conventional raster scan display formats. The output of the scan converter 928 is supplied to a display 930, which displays an image of the region of interest in the patient's body.

A system controller 932 provides overall control of the ultrasound imaging system 900. The system controller 932 performs timing and control functions and typically includes a microprocessor operating under the control of graphics generator 936 and control routines 942, both contained within data storage 940. When the desired ultrasound image is communicated to the system controller 932, the system controller 932, in cooperation with the control routines 942 and the graphics generator 936, determines the appropriate scan lines that should be projected by the ultrasound probe 950 to achieve the desired ultrasound image communicated to the system controller 932 and displayed at display 930.

The control routines 942 can include standard routines that are typically found in ultrasound systems, such as, but not limited to, spectral Doppler image processing 944, color Doppler image processing 946, and two-dimensional (2D) image processing 948. However, in the ultrasound imaging system 900, the control routines 942 further include a user guiding algorithm 950 and a health analysis algorithm 952 for use with the ultrasound-detectable marker 100.

Namely, the user guiding algorithm 950 is used during surgery when the ultrasound-detectable marker 100 is placed in the patient. Further, the user guiding algorithm 950 is used postoperatively to guide the user to locate the vascular anastomosis site or the postoperative site (i.e., locate the ultrasound-detectable marker 100) for monitoring vascular flow and patency. More details of the user guiding algorithm 950 are described herein below with reference to FIG. 14. The health analysis algorithm 952 is used to measure and display flow data from at least one vessel. More details of the health analysis algorithm 952 are described herein below with reference to FIG. 15.

Accordingly, using the user guiding algorithm 950 and the health analysis algorithm 952, the ultrasound imaging system 900 provides images and quantitative analysis of the vasculature to determine patency and volumetric flow rate, thus indicating the overall health of the tissue site.

III. Methods of Monitoring Vascular Flow and Patency Under Ultrasound

The design of the presently disclosed ultrasound-detectable marker 100 provides feedback to the user to help orient an ultrasound probe properly via a specific ultrasound signature. In one embodiment, the ultrasound-detectable marker 100 is placed underneath a vessel at the site of anastomosis in a reconstructive surgical procedure that involves joining two vessels, such as shown in FIG. 6, FIG. 7, and FIG. 8. Placement of the ultrasound-detectable marker 100 can be accomplished by suturing the ultrasound-detectable marker 100 to soft tissue adjacent to the vessel, by using an adhesive, or by a hooking mechanism. In embodiments involving suturing, holes and/or slits (e.g., holes and/or slits 115 shown in FIG. 1 and FIG. 2) or small eyelets (e.g., eyelets 120 shown in FIG. 4) can be provided in the ultrasound-detectable marker 100. In other embodiments, the ultrasound-detectable marker 100 is placed adjacent to the one or more vessels or above one or more vessels.

The presently disclosed ultrasound-detectable marker 100 can be used postoperatively during an ultrasound exam to guide the positioning of the probe (e.g., ultrasound probe 950) until the postoperative site, such as an anastomosis site, is found. This navigation process can be performed using the geometric marker feedback independently, or it can be performed with the aid of software; namely, the user guiding algorithm 950 and/or the health analysis algorithm 952. At this point, the medical personnel operating the ultrasound (e.g., ultrasound imaging system 900) is able to capture images of the vessels both axially and longitudinally, in addition to gathering vessel parameters, including vessel lumen patency and blood flow rate, using the color Doppler function (e.g., color Doppler image processing 946) inherent in ultrasound machines known in the art.

In reconstructive surgery applications, such as microvascular reconstruction or "free flap" surgery, this information allows for accurate examination of vessel function postoperatively to assess the overall health of the reconstructed tissue and indicate whether clinical actions should be taken. While many methods of solving the problem of monitoring the reconstructed tissue's health have been tried, none permit the direct visualization of flow and all suffer from drawbacks that have prevented any single technology from gaining predominant use (see Smit J M, Zeebregts C J, Acosta R, Werker P M. Advancements in free flap monitoring in the last decade: a critical review. *Plast Reconstr Surg*. January 2010; 125(1):177-185). More particularly, the presently disclosed ultrasound-detectable marker 100 and methods may allow detection of clots upon formation well before complete occlusion occurs. Both clinical examination and existing technologies frequently only detect complete vessel blockage, by which time it may be too late to restore blood flow and salvage the surgery (see Gimbel M L, Rollins M D, Fukaya E, Hopf H W. Monitoring partial and full venous outflow compromise in a rabbit skin flap model. *Plast Reconstr Surg*. September 2009; 124(3):796-803). The presently disclosed ultrasound-detectable marker 100 and methods also can be useful in transplant and vascular surgeries, as well as in procedures involving urology.

Representative examples illustrating the use of the presently disclosed ultrasound-detectable marker 100 are provided in FIGS. 10 and 11. Referring now to FIG. 10, is shown an vascular anastomosis site 1000 in which a pair of postoperative vessels 1010 can naturally adopt a tortuous course, which is not amenable to cross-sectional visualization and imaging. In contrast, referring now to FIG. 11, the presently disclosed ultrasound-detectable marker 100 aligns the postoperative vessels 1010 to permit visualization, as shown in in vivo swine ultrasound images where an artery and vein are easily observed inside the echogenic marker, e.g., the presently disclosed ultrasound-detectable marker 100 (e.g., see inset showing a frame 1020 of an ultrasound image).

Accordingly, in some embodiments, the presently disclosed subject matter provides a method for monitoring a vascular anastomosis site. In particular embodiments, the methods are used to monitor a vascular anastomosis site after surgery. For example, FIG. 12 illustrates a flow diagram of an example of a method 1200 of monitoring a vascular anastomosis site during surgery or post-surgery using the ultrasound-detectable marker 100 and the ultrasound imaging system 900. The method 1200 incudes, but it not limited to, the following steps.

At a step 1210, the ultrasound-detectable marker 100 that comprises one or more resorbable polymers is provided, wherein the ultrasound-detectable marker 100 is adapted for placement underneath, adjacent to, or above one or more vessels at a vascular anastomosis site.

At a step 1215, the ultrasound-detectable marker 100 is placed underneath, adjacent to, or above at least one vessel during or after surgery.

At a step 1220, the user guiding algorithm 950 is used postoperatively to guide a user with an ultrasound probe to the location of the ultrasound-detectable marker 100.

In yet other embodiments, the presently disclosed subject matter provides a method for orienting at least one vessel linearly in a plane during surgery. For example, FIG. 13 illustrates a flow diagram of an example of a method 1300 of orienting at least one vessel linearly in a plane during surgery using the ultrasound-detectable marker 100 and the ultrasound imaging system 900. The method 1300 incudes, but it not limited to, the following steps.

At a step 1310, the ultrasound-detectable marker 100 that comprises one or more resorbable polymers is provided, wherein the ultrasound-detectable marker 100 is adapted for placement underneath, adjacent to, or above one or more vessels at a vascular anastomosis site.

At a step 1315, the ultrasound-detectable marker 100 is placed in a subject during surgery. Namely, the ultrasound-detectable marker 100 is placed underneath, adjacent to, or above at least one vessel during surgery.

At a step 1320, the one or more vessels are placed on the ultrasound-detectable marker 100, wherein the one or more vessels are oriented linearly in a plane after being placed on the ultrasound-detectable marker 100.

In other embodiments, the methods further comprise using the user guiding algorithm 950 of the ultrasound imaging system 900 of FIG. 9 to guide the user with respect to locating the ultrasound-detectable marker 100 via ultrasound. For example, FIG. 14 illustrates a flow diagram of an example of the process flow 1400 of the user guiding algorithm 950 of the ultrasound imaging system 900. The process flow 1400 incudes, but it not limited to, the following steps.

At a step 1410, ultrasound waves are generated via, for example, the pulse generator 916, the transmit beamformer 910, the T/R switch 912, and the ultrasound probe 950.

At a step 1415, the reflected ultrasound waves are received with a transducer; namely, via the ultrasound probe 950 and the ultrasound receiver 926.

At a step 1420, using, for example, the signal processor 924 and the system controller 932, at least one B-mode image is generated. As used herein, the term "B-mode" refers to a two-dimensional cross section of the tissue being imaged. More particularly, the term "B-mode" refers to a two-dimensional ultrasound presentation of echo-producing interfaces in a single plane.

At a step 1425, using, for example, the signal processor 924 and the system controller 932, the at least one B-mode image is segmented. As used herein, the term "segmented" refers to the process of partitioning a digital image into multiple segments, e.g., sets of pixels. Such image segmentation can be used to simplify and/or change the representation of an image and is typically used to locate objects and boundaries, e.g., lines, curves, and the like, in images. More particularly, image segmentation is the process of assigning a label to every pixel in an image such that pixels having the same label share certain visual characteristics. The end result of image segmentation is a set of segments that collectively cover the entire image, or a set of contours extracted from the image.

At a step 1430, using, for example, the system controller 932 and/or the user guiding algorithm 950, a template is matched to the defined marker shape. As used herein, the process of "template matching," as in when a template is matched to the defined marker shape, refers to a technique in digital image processing for finding small parts of an image that match a template image, for example, as a way to detect edges in an image. If the template image has strong features, a feature-based approach can be used. For templates that do not have strong features, or under circumstances when the bulk of the template image constitutes the matching image, a template-based approach can be used. In instances when the template might not provide a direct match, eigenspaces, e.g., templates that detail the matching object under a number of different conditions including, but not limited to, varying perspectives, illuminations, color contrasts, or acceptable matching poses, can be used. In some embodiments, the process of template matching uses a convolution mask, i.e., a template, tailored to a special feature of the search image to be detected.

For example, in representative embodiments, such a method can be implemented by first choosing a part of the search image to use as a template, which can be referred to as the search image $S(x, y)$, where $(x, y)$ represent the coordinates of each pixel in the search image. The template can be represented as $T(x_t, y_t)$, where $(x_t, y_t)$ represents the coordinates of each pixel in the template. The center (or the origin) of template $T(x_t, y_t)$ can then be moved over each $(x, y)$ point in the search image and the sum of products can be calculated between the coefficients in $S(x, y)$ and $T(x_t, y_t)$ over the whole area spanned by the template. As all possible positions of the template with respect to the search image are considered, the position with the highest score is the best position.

At a step 1435, using, for example, the system controller 932 and/or the user guiding algorithm 950, a pose is estimated. By "pose," is meant the combination of position and orientation of an object. The pose of an object is generally determined using image data. In some embodiments, the pose is described by means of a rotation and translation transformation, which brings the object from a reference pose to the observed pose. The pose estimation is performed to determine how the transducer and marker are positioned relative to each other. For example, the pose estimation may determine that the transducer is currently seeing a rotated view of the marker.

At a step 1440, using, for example, the system controller 932 and/or the user guiding algorithm 950, a desired pose is calculated. The "desired pose" is the relative positioning of marker and transducer that one wishes to achieve. This position could be either the very center of the marker (i.e., no translation or rotation), or it could simply be that the desired pose is the same transducer/marker relation at which earlier flow measurements were taken and it is desirable to take new measurements at exactly the same view on the ultrasound.

At a step 1445, using, for example, the system controller 932 and/or the user guiding algorithm 950, guidance is provided to the user with respect to repositioning the ultrasound probe 950 based on the desired pose. Guidance can be provided by either a display of the marker shape on which the cross-sectional view that the ultrasound is currently observing is labeled or highlighted or by stepwise corrective instructions to achieve the desired pose (e.g., rotate the transducer 30 degrees clockwise, move one cm forward, and the like).

In still other embodiments of the process flow 1400, more than one B-mode image is generated and segmented before matching a template to the defined marker shape. In further embodiments, the process flow 1400 can be repeated until the ultrasound probe 950 is positioned so that the desired pose is observed.

In some embodiments, the methods further comprise using the health analysis algorithm 952 of the ultrasound imaging system 900 to measure and display flow data from at least one vessel. For example, FIG. 15 illustrates a flow diagram of an example of the process flow 1500 of the health analysis algorithm 952 of the ultrasound imaging system 900. The process flow 1500 incudes, but it not limited to, the following steps.

At a step 1510, ultrasound waves are generated via, for example, the pulse generator 916, the transmit beamformer 910, the T/R switch 912, and the ultrasound probe 950.

At a step 1515, the reflected ultrasound waves are received with a transducer; namely, via the ultrasound probe 950 and the ultrasound receiver 926.

At a step 1520, using, for example, the system controller 932 and/or the health analysis algorithm 952, the desired pose may optionally be confirmed. This step is optional. Pose estimation (as per above) can be performed again to confirm that the position is as desired prior to beginning doppler data collection. For example, if the user was guided to the center of the marker by the guidance algorithm, but then moved the probe prior to starting collection of the flow data, inaccurate data could be obtained. Performing one more pose estimation as part of the Doppler flow data collection process allows confirmation of pose, as well as recording of the location (pose) at which the data were collected.

At a step 1525, using, for example, the system controller 932 and/or the health analysis algorithm 952, at least one B-mode image and at least one set of Doppler velocities are collected via, for example, spectral Doppler image processing 944 and color Doppler image processing 946.

At a step 1530, using, for example, the system controller 932 and/or the health analysis algorithm 952, a power signal is spatially analyzed to define the X/Y boundaries of the at least one blood vessel.

At a step 1535, using, for example, the system controller 932 and/or the health analysis algorithm 952, multiple frames are temporally analyzed to differentiate the at least one vessel from another vessel.

At a step 1540, using, for example, the system controller 932 and/or the health analysis algorithm 952, individual Doppler velocities are integrated over the calculated X/Y boundaries of the at least one vessel.

At a step 1545, using, for example, the system controller 932 and/or the health analysis algorithm 952, the multiple frames are averaged.

At a step 1550, the integrated, averaged Doppler velocities are quantitatively displayed to the user via display 930 or otherwise indicated to the user.

Figure 16:
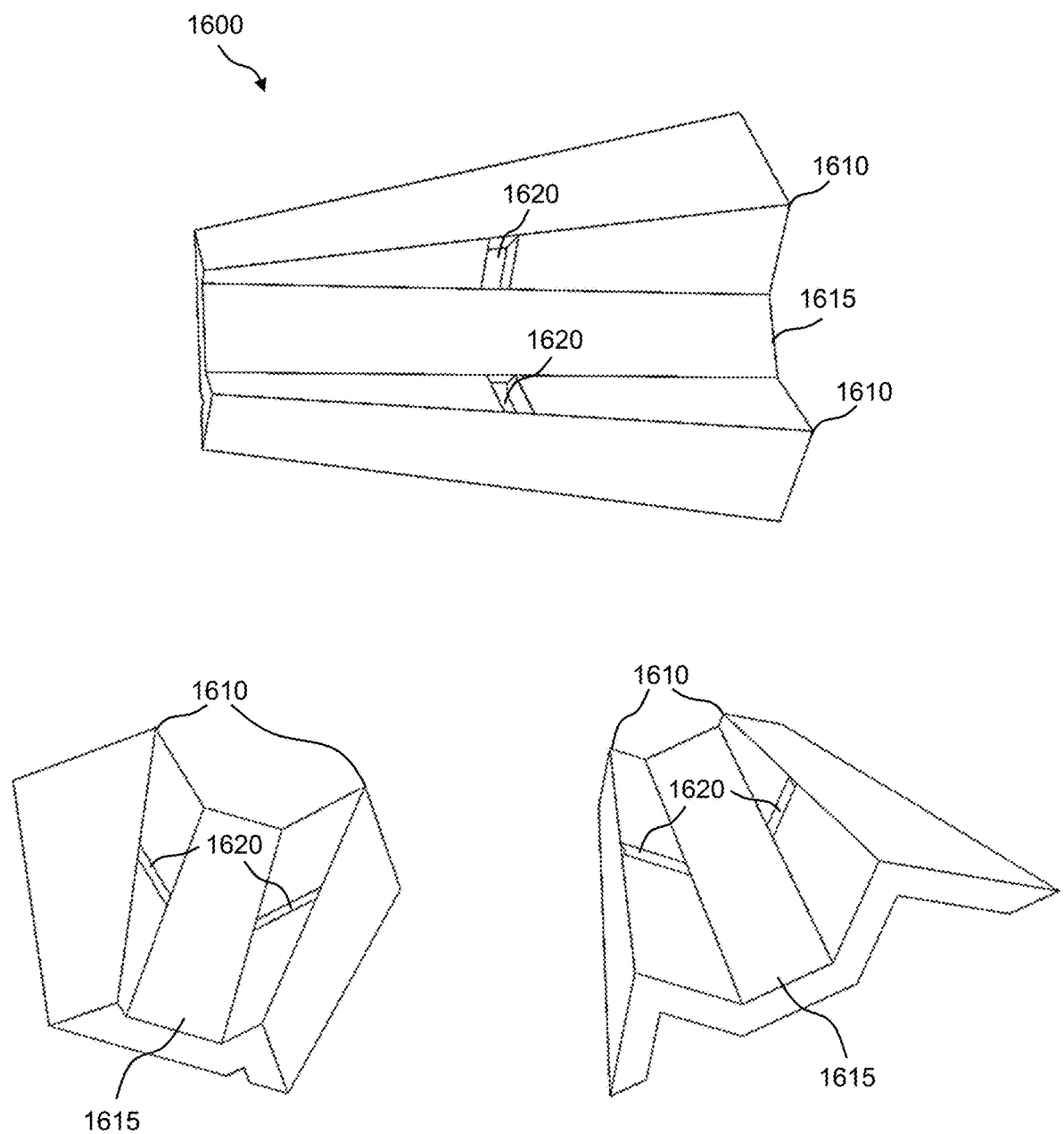

Referring now to FIG. 16, FIG. 17, FIG. 18, and FIG. 19 are various views of yet other examples of the presently disclosed ultrasound-detectable markers. Namely, FIG. 16 shows various perspective views of an ultrasound-detectable marker 1600. The body of the ultrasound-detectable marker 1600 comprises a pair of ridges 1610, which flank a trough 1615. This arrangement provides a channel in which one or more vessels may rest. The body of the ultrasound-detectable marker 1600 also comprises holes and/or slits 1620. In this example, the overall footprint of the ultrasound-detectable marker 1600 has a taper from one end to the other. In other words, one end of the ultrasound-detectable marker 1600 is narrower than the other end, as shown.

Figure 17:
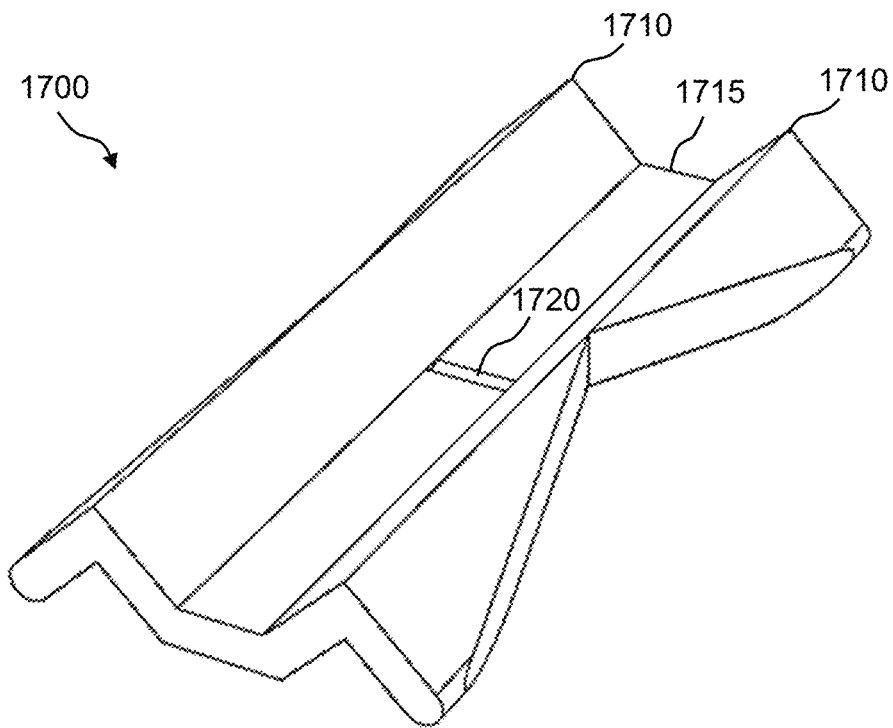
Figure 17:
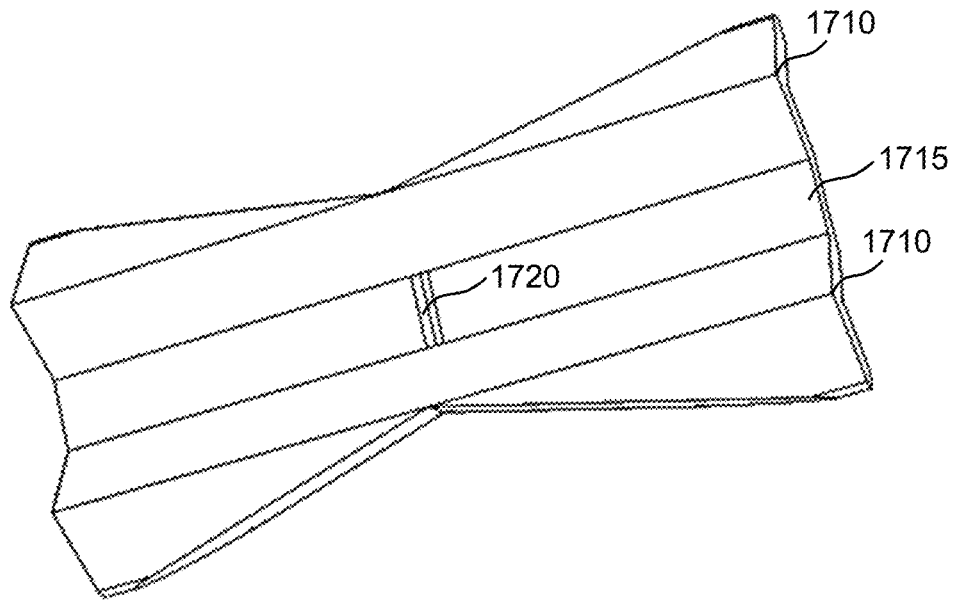

FIG. 17 shows various perspective views of an ultrasound-detectable marker 1700. The body of the ultrasound-detectable marker 1700 comprises a pair of ridges 1710, which flank a trough 1715. This arrangement provides a channel in which one or more vessels may rest. The body of the ultrasound-detectable marker 1700 also comprises a hole and/or slit 1720. In this example, the overall footprint of the ultrasound-detectable marker 1700 has an hourglass-type of shape. In other words, the middle region of the ultrasound-detectable marker 1700 is narrower than the end regions, as shown.

Figure 18:
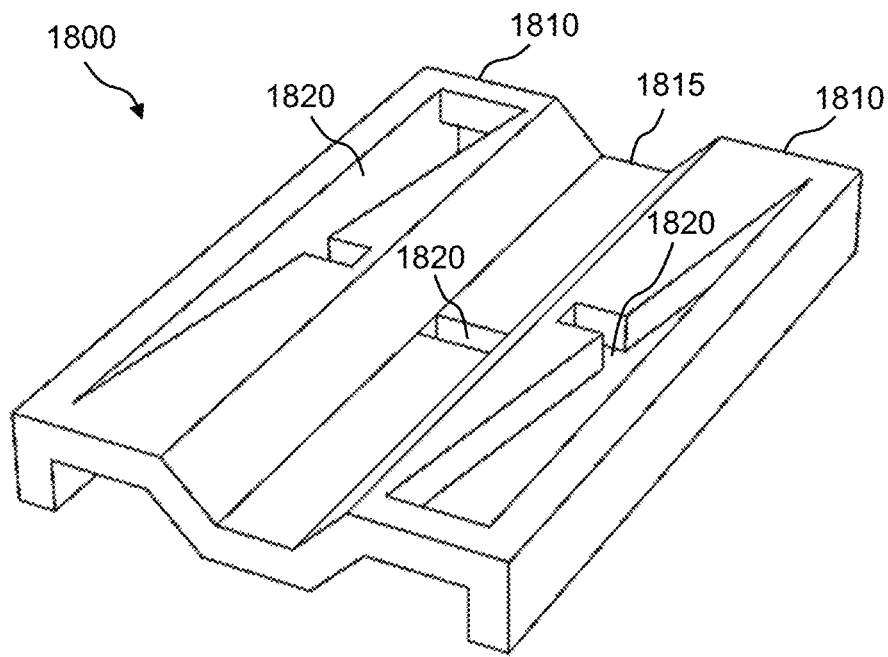
Figure 18:
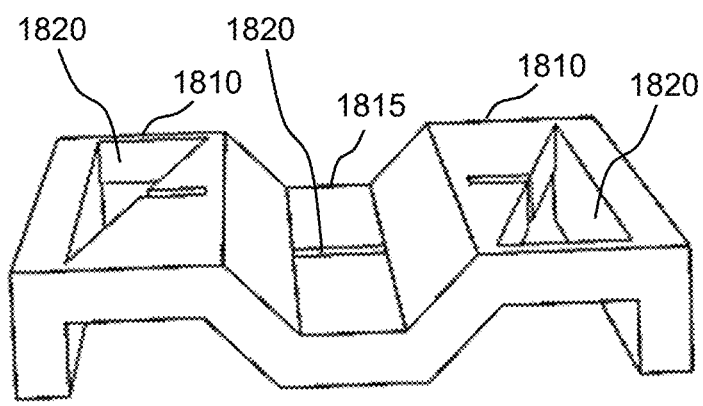

FIG. 18 shows various perspective views of an ultrasound-detectable marker 1800. The body of the ultrasound-detectable marker 1800 comprises a pair of plateaus 1810, which flank a trough 1815. This arrangement provides a channel in which one or more vessels may rest. The body of the ultrasound-detectable marker 1800 also comprises holes and/or slits 1820. In this example, the ultrasound-detectable marker 1800 has a rectangular table-like structure, as shown.

Figure 19:
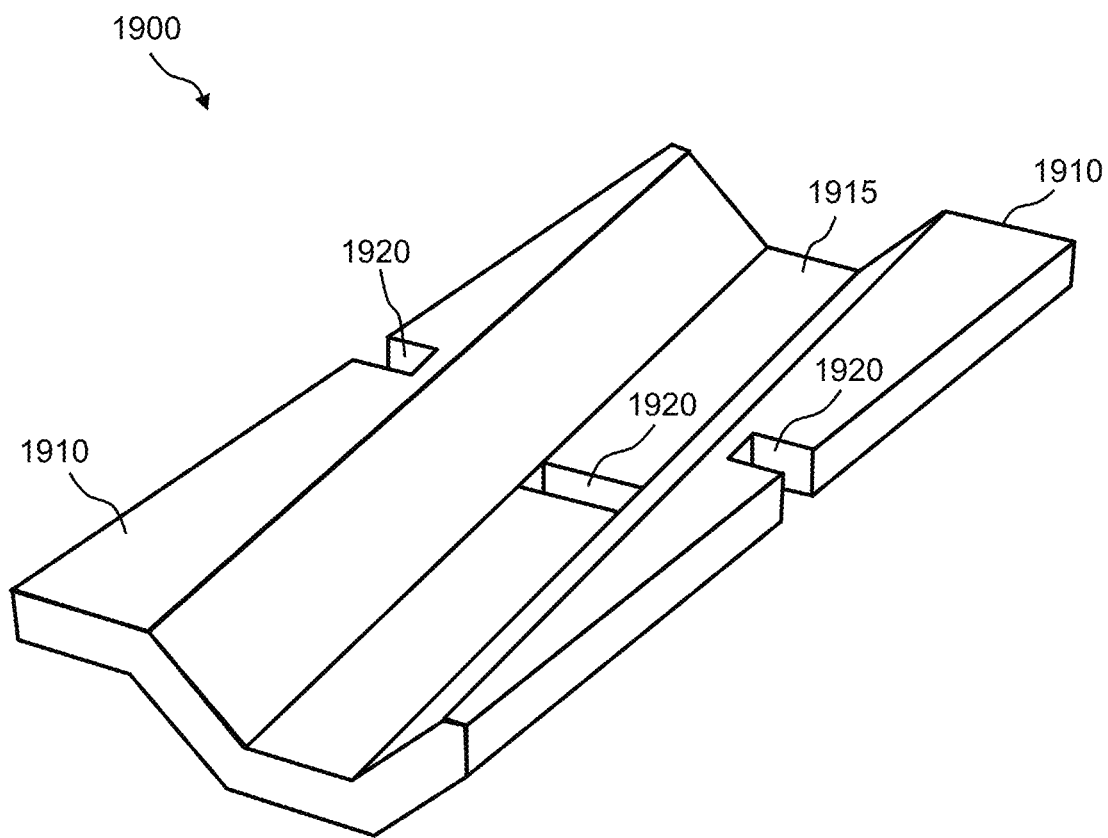

FIG. 19 shows a perspective view of an ultrasound-detectable marker 1900. The body of the ultrasound-detectable marker 1900 comprises a pair of plateaus 1910, which flank a trough 1915. This arrangement provides a channel in which one or more vessels may rest. The body of the ultrasound-detectable marker 1900 also comprises holes and/or slits 1920. In this example, the ultrasound-detectable marker 1900 has a rectangular plate-like structure, as shown.

As described with reference to the ultrasound-detectable markers 100 shown in FIG. 1 through FIG. 8, the ultrasound-detectable markers 1600, 1700, 1800, 1900 comprise one or more resorbable polymers, one or more non-resorbable polymers, one or more non-polymeric materials, or any combinations thereof.

In other embodiments, the presently disclosed methods comprise determining a patency and/or a vascular health of at least one vessel. In further embodiments, determining a patency and/or a vascular health of at least one vessel comprises detecting a blood clot before complete occlusion occurs.

The subject treated by the presently disclosed methods in their many embodiments is desirably a human subject, although it is to be understood that the methods described herein are effective with respect to all vertebrate species, which are intended to be included in the term "subject."

A "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by That which is claimed:

1. An ultrasound-detectable marker for monitoring a postoperative site, wherein the ultrasound-detectable marker comprises a material selected from one or more resorbable polymers, one or more non-resorbable polymers, one or more nonpolymeric materials, or any combinations thereof; and wherein the ultrasound-detectable marker comprises a channel which can accommodate a portion of one or more vessels therein and wherein the portion of the one or more vessels is ultrasonically imageable when accommodated by the ultrasound-detectable marker.

2. The ultrasound-detectable marker of claim 1, wherein the channel is defined by a pair of ridges or plateaus flanking a trough.

3. The ultrasound-detectable marker of claim 1, wherein the ultrasound-detectable marker has a taper from one end to the other.

4. The ultrasound-detectable marker of claim 3, wherein the taper of the ultrasound-marker yields one or more cross-sectional images which provide specificity as to which area of the marker is being insonated and from which angle.

5. The ultrasound-detectable marker of claim 1, wherein the ultrasound-detectable marker comprises one or more resorbable polymers selected from the group consisting of poly(lactic-co-glycolic acid) (PLGA), a polylactide (PLA), polyglycolide (PGA), polycaprolactone, a polyhydroxyalkanoate (PHA), polydioxanone, polyethylene glycol, collagen, hyaluronate, L-lactide/caprolactone, and copolymers thereof.

6. The ultrasound-detectable marker of claim 5, wherein the one or more resorbable polymers is selected from the group consisting of PLA, PGA, polycaprolactone, and copolymers thereof.

7. The ultrasound-detectable marker of claim 5, wherein the one or more resorbable polymers is PLGA or L-lactide/caprolactone.

8. The ultrasound-detectable marker of claim 7, wherein the presence of two or more resorbable polymer layers and/or a varying ratio of two or more resorbable polymers creates an impedance change throughout the marker.

9. The ultrasound-detectable marker of claim 1, wherein the ultrasound-detectable marker comprises two or more resorbable polymer layers, wherein at least two resorbable polymer layers do not comprise the same resorbable polymer.

10. The ultrasound-detectable marker of claim 9, wherein the two resorbable polymer layers are selected from the group consisting of PLA, PGA, polycaprolactone, and copolymers thereof.

11. The ultrasound-detectable marker of claim 1, wherein the ultrasound-detectable marker comprises a varying ratio of two or more resorbable polymers.

12. The ultrasound-detectable marker of claim 11, wherein the ultrasound-detectable marker comprises a varying ratio of PLA:PGA or PLA:polycaprolactone.

13. The ultrasound-detectable marker of claim 1, wherein the ultrasound-detectable marker comprises one or more non-resorbable polymers.

14. The ultrasound-detectable marker of claim 13, wherein the one or more nonresorbable polymers is selected from the group consisting of polycarbonate, polyetheretherketone, polypropylene, silicone, polyethylene, and combinations thereof.

15. The ultrasound-detectable marker of claim 1, wherein the ultrasound-detectable marker comprises at least one eyelet hole adapted to secure the ultrasound-detectable marker to soft tissue near the postoperative site.

16. The ultrasound-detectable marker of claim 1, wherein the one or more vessels are selected from an artery and a vein.

17. The ultrasound-detectable marker of claim 1, wherein the ultrasound-detectable marker has a detectable in vivo lifetime during which the ultrasound-detectable marker remains detectable by ultrasound.

18. The ultrasound-detectable marker of claim 1, wherein the postoperative site comprises or is near a vascular anastomosis site.

19. A method for monitoring a postoperative site, the method comprising: (a) providing an ultrasound-detectable marker of claim 1; (b) placing the ultrasound-detectable marker underneath, adjacent to, or above one or more vessels during or after surgery; and (c) using a software algorithm to guide a user with an ultrasound probe to the location of the ultrasound-detectable marker post-surgery.

20. The method of claim 19, wherein using the software algorithm comprises one or more of: (a) generating ultrasound waves; (b) receiving reflected ultrasound waves with a transducer; (c) generating at least one B-mode image; (d) segmenting the at least one B-mode image; (e) matching a template to the defined marker shape; (f) estimating a pose; and (g) calculating a desired pose.

21. The method of claim 20, further comprising giving a user guidance on repositioning the probe based on the desired pose.

22. The method of claim 20, wherein the method is repeated until the probe is positioned so that the desired pose is observed, wherein the desired pose falls within a range of acceptable poses.

23. The method of claim 20, wherein more than one B-mode image is generated and segmented before matching a template to the defined marker shape.

24. The method of claim 19, further comprising using a second software algorithm to measure and display flow data from the at least one vessel.

25. The method of claim 24, wherein using the second software algorithm comprises one or more of: (a) generating ultrasound waves; (b) receiving reflected ultrasound waves with a transducer; (c) confirming the desired pose; (d) collecting at least one B-mode image and at least one set of Doppler data including velocity information; (e) spatially analyzing one or more of Doppler data or a B-mode image to calculate X/Y boundaries of the at least one vessel; (f) integrating individual Doppler velocities over the calculated X/Y boundaries of the at least one vessel; (g) averaging over the collected frames; and (h) quantitatively displaying the integrated, averaged Doppler velocities.

26. The method of claim 19, comprising determining a patency and/or a vascular health of the at least one vessel.

27. The method of claim 26, wherein the determining a patency and/or a vascular health of the at least one vessel comprises detecting a blood clot before complete occlusion occurs or other characteristic of vessel health associated with vascular flow and/or patency.

28. The method of claim 19, wherein the ultrasound-detectable marker comprises two or more resorbable polymer layers and/or a varying ratio of two or more resorbable polymers and wherein the presence of two or more resorbable polymer layers and/or a varying ratio of two or more resorbable polymers creates an impedance change throughout the ultrasound-detectable marker.

29. A method for orienting at least one vessel during surgery, the method comprising: (a) providing an ultrasound-detectable marker of claim 1; (b) placing the ultrasound-detectable marker in a subject during surgery; and (c) placing the at least one vessel on the ultrasound-detectable marker; and wherein the at least one vessel is oriented after being accommodated by the ultrasound-detectable marker.

30. The method of claim 29, wherein the at least one vessel is oriented in a parallel direction with respect to the channel after being accommodated by the ultrasound-detectable marker.

31. The method of claim 29, further comprising attaching the ultrasound-detectable marker to soft tissue adjacent to the postoperative site.

32. The method of claim 31, wherein attaching the ultrasound-detectable marker to soft tissue occurs by at least one method selected from the group consisting of suturing, using an adhesive, a mechanical stapler, a biodegradable or resorbable glue, and using a hooking mechanism.

33. The method of claim 29, wherein the ultrasound-detectable marker comprises two or more resorbable polymer layers and/or a varying ratio of two or more resorbable polymers and wherein the presence of two or more resorbable polymer layers and/or a varying ratio of two or more resorbable polymers creates an impedance change throughout the ultrasound-detectable marker.

\* \* \* \* \*